United States Patent [19]
Gordon et al.

[11] Patent Number: 5,745,542
[45] Date of Patent: Apr. 28, 1998

[54] RING SUPPRESSION FILTER FOR USE IN COMPUTED TOMOGRAPHY SYSTEMS

[75] Inventors: Bernard M. Gordon, Magnolia; Lai Ching-Ming, Wakefield, both of Mass.

[73] Assignee: Analogic Corporation, Peabody, Mass.

[21] Appl. No.: 840,367

[22] Filed: Apr. 29, 1997

Related U.S. Application Data

[63] Continuation of Ser. No. 614,541, Mar. 31, 1996, abandoned.
[51] Int. Cl.$^6$ .................................................. A61B 6/03
[52] U.S. Cl. ........................................ 378/4; 378/901
[58] Field of Search ............................. 378/4, 15, 901; 364/413.15, 413.16

[56] References Cited

U.S. PATENT DOCUMENTS

| | | | |
|---|---|---|---|
| 4,670,840 | 6/1987 | Freundlich | 364/413.19 |
| 5,473,656 | 12/1995 | Hsieh et al. | 378/4 |
| 5,533,081 | 7/1996 | Hsieh | 378/15 |

OTHER PUBLICATIONS

Jiang Hsieh, *Image Artifacts, Causes and Correction*, Medical CT & Ultrasound: Current Technology and Applications (Goldman et al., ed.) Advanced Medical Publishing (1995) pp. 487–517.

Kowalski, Suppression of Ring Artefacts in CT Fan–Beam Scanners, IEEE, vol. NS–25, No. 5, pp. 1111–1116, Oct. 1978.

*Primary Examiner*—David P. Porta
*Assistant Examiner*—David Vernon Bruce
*Attorney, Agent, or Firm*—Lappin & Kusmer LLP

[57] ABSTRACT

A computed tomography (CT) system utilizes a ring suppression filter for suppressing ring artifacts in a CT image. The system generates projections at a plurality of projection angles, and each projection includes one measurement of a plurality of projection data signals. The ring suppression filter includes a high pass filter, a histogram generator, and a combiner. The high pass filter generates a measurement of an error signal corresponding to each of the measurements of one of the projection data signals, and each of the error signal measurements is representative of the high frequency components in a portion of one of the projections. The histogram generator generates a histogram signal representative of a relationship between the measurements of the error signal and the measurements of the projection data signal. The combiner combines the measurements of the error signal and the histogram signal to generate a plurality of measurements of a ring corrected signal.

43 Claims, 10 Drawing Sheets

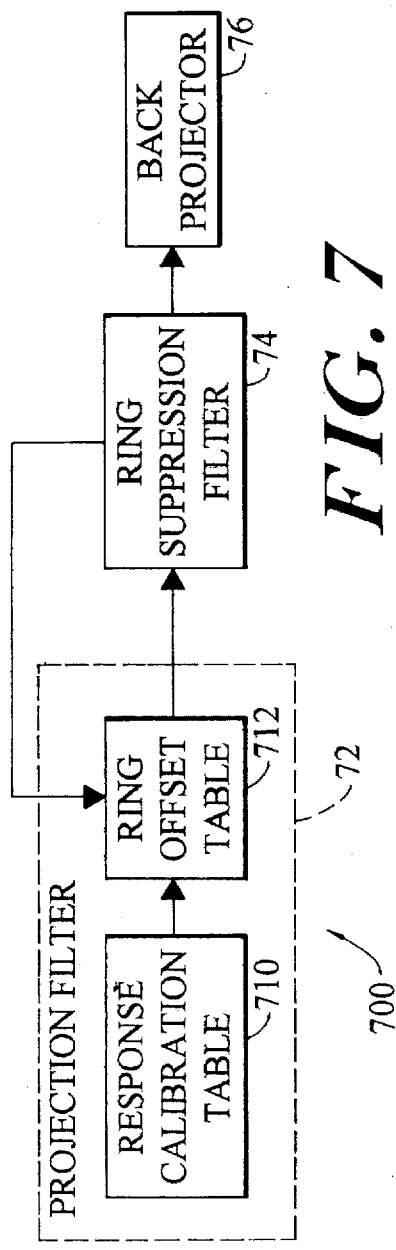
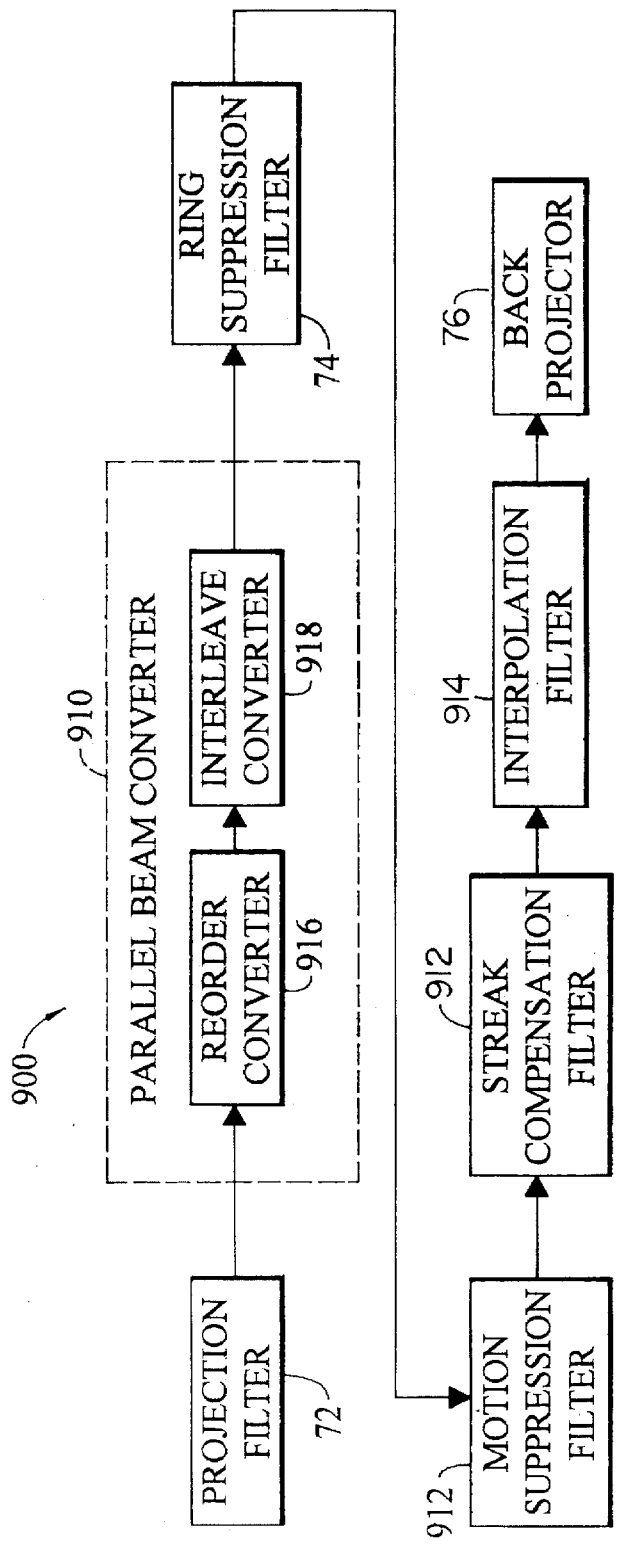

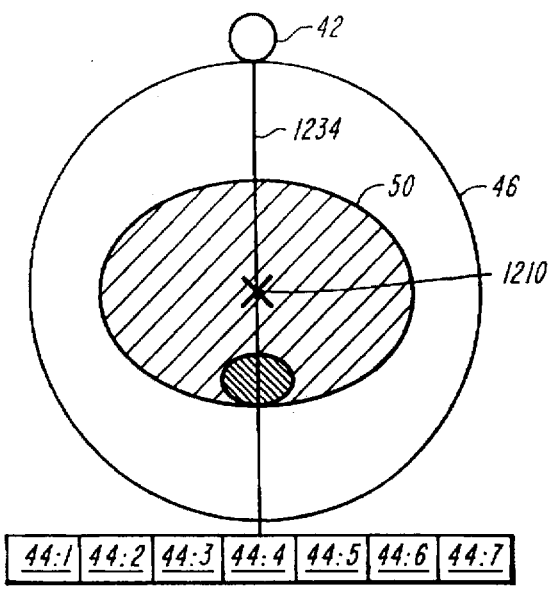
FIG. 11A
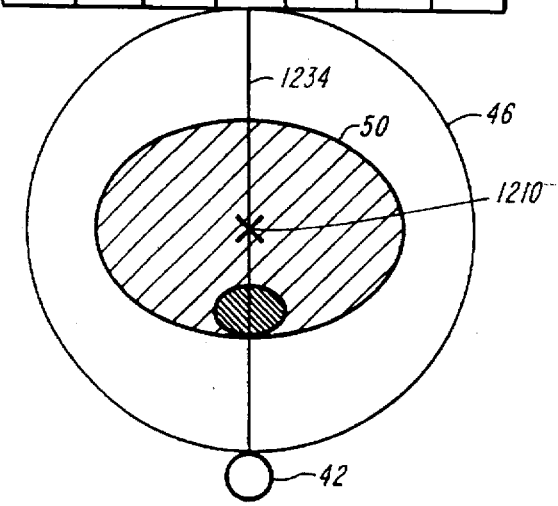
FIG. 11B
FIG. 12

RING SUPPRESSION FILTER FOR USE IN COMPUTED TOMOGRAPHY SYSTEMS

This is a continuation application of application Ser. No. 08/614,541 filed on Mar. 31, 1996, now abandoned.

CROSS-REFERENCE TO RELATED APPLICATIONS

This application is related to U.S. patent application Ser. No. 08/587,468 entitled STREAK SUPPRESSION FILTER FOR USE IN COMPUTED TOMOGRAPHY SYSTEMS, assigned to the present assignee, and filed on Jan. 17, 1996, which is hereby incorporated by reference, and to U.S. patent application Ser. No. 08/614,623, entitled MOTION ARTIFACT SUPPRESSION FILTER FOR USE IN COMPUTED TOMOGRAPHY SYSTEMS, assigned to the present assignee, and filed on Mar. 13, 1996, which is hereby incorporated by reference, and to U.S. patent application Ser. No. 08/614,660, entitled SELF CALIBRATING RING SUPPRESSION FILTER FOR USE IN COMPUTED TOMOGRAPHY SYSTEMS, assigned to the present assignee, and filed on Mar. 13, 1996, which is hereby incorporated by reference.

FIELD OF THE INVENTION

The present invention relates generally to Computed Tomography (CT) systems used in the medical arts for generating CT images of, for example, human patients. More particularly, the invention relates to an improved ring suppression filter for reducing rings in CT images.

BACKGROUND OF THE INVENTION

CT systems of the third generation type include an X-ray source and an X-ray detector system secured respectively to diametrically opposite sides of an annular-shaped disk. The disk is rotatably mounted within a gantry support so that during a scan, the disk continuously rotates about a rotation axis while X-rays pass from the secure through an object positioned within the opening of the disk to the detector system.

The detector system typically includes an array of detectors disposed as a single row in the shape of an arc of a circle having a center of curvature at the point, referred to as the "focal spot", where the radiation emanates from the X-ray source. The X-ray source and the array of detectors are positioned so that the X-ray paths between the source and each detector all lie in the same plane (hereinafter the "slice plane" or "scanning plane") which is normal to the rotation axis of the disk. Since the X-ray paths originate from what is substantially a point source and extend at different angles to the detectors, the X-ray paths resemble a fan, and thus the term "fan beam" is frequently used to describe all of the X-ray paths at any one instant of time. The X-rays incident on a single detector at a measuring instant during a scan are commonly referred to as a "ray", and each detector generates an output signal indicative of the intensity of its corresponding ray. Each ray is partially attenuated by all the mass in its path. The output signal generated by each detector in fact is representative of and a function of the density of all the mass disposed between that detector and the X-ray source (i.e., the density of the mass lying in the detector's corresponding ray path).

The output signals generated by the X-ray detectors are normally processed by a signal processing portion of the CT system. The signal processing portion generally includes a data acquisition system (DAS) which filters the output signals generated by the X-ray detectors to improve their signal-to-noise ratio. The filtered output signals generated by the DAS are commonly referred to as "raw data signals". The signal processing portion usually includes a projection filter which logarithmically processes the raw data signals to generate a set of projection data signals so that each projection data signal is representative of the density of the mass lying in a corresponding ray path. The collection of all the projection data signals at a measuring instant is commonly referred to as a "projection" or a "view". During a single scan, as the disk rotates, a plurality of projections are generated such that each projection is generated at a different angular position of the disk. The angular orientation of the source and detectors on the disk corresponding to a particular projection is referred to as the "projection angle".

Using well known algorithms, such as the Radon algorithm, a CT image may be generated from all the projection data signals collected at each of the projection angles. A CT image is representative of the density of a two dimensional "slice", along the scanning plane, of the object being scanned. The process of generating a CT image from the projection data signals is commonly referred to as "filtered back projection" or "reconstruction", since the CT image may be thought of as being reconstructed from the projection data. The signal processing portion of the CT system normally includes a back projector for generating the reconstructed CT images from the projection data signals.

One problem with CT systems is that a variety of noise and error sources may potentially contribute noise or artifacts to the reconstructed CT images. CT systems therefore typically employ a host of signal processing techniques to improve the signal-to-noise ratio and to reduce the presence of artifacts in the reconstructed CT images.

One important factor which can cause unwanted artifacts to appear in the reconstructed CT images relates to the uniformity and stability of the X-ray detectors. If a single detector is out of calibration with respect to the other detectors in the array, the single detector will cause an artifact to appear in the reconstructed CT image having the appearance of a circular ring, or one or more circular arcs, centered about the "center" of the reconstructed CT image (where the "center" of the reconstructed CT image corresponds to the location of the rotation axis of the disk). If more than one detector is out of calibration, they collectively cause a group of concentric circular rings or circular arcs to appear in the reconstructed CT image. Such artifacts are typically referred to as "rings", and "deringing" or "ring suppression" refers to methods and apparatus for reducing or eliminating the appearance of rings in the reconstructed CT images.

Ideally, the X-ray detectors are constructed so that their transfer functions, or more simply their "responses", are all equal, however, this is difficult to achieve in practice. In many CT systems, the projection filter contains a "response calibration table" which is used to adjust the projection data signals to compensate for differences in the detector responses. The response calibration table is typically generated by scanning objects of known density, often referred to as "phantoms", and the response calibration table is updated periodically. Such response calibration tables are generally effective at suppressing rings immediately after the tables are updated. However, detector responses tend to drift over time due to temperature variations and radiation damage, as well as other factors, and it is generally difficult to insure that the response of any single detector will remain within a given tolerance of the other detectors. Frequently, the response of one or more detectors drifts enough between updates of the response calibration table to cause rings to appear in the reconstructed CT images.

FIG. 1 is a reconstructed CT image of a human head that is illustrative of the problems associated with rings. As those skilled in the art will appreciate, the CT image shown in FIG. 1 contains rings which interfere with interpretation of the image.

Prior art methods of suppressing rings typically involve high pass filtering the projection data signals to generate a set of high frequency signals and then averaging the high frequency signals over a number of adjacent projection angles to determine an offset for each detector. Each high frequency signal may be thought of as containing an error component superimposed on a data component (where the data component represents the high frequency components of a density profile of the patient and the error component represents an offset in the response of a detector relative to the other detectors). Since the data component is somewhat random when viewed over many projection angles and the error component tends to remain somewhat constant, averaging the high frequency signals tends to cancel out the data components leaving only the error component. The averaged signals are then used as offset values to adjust the projection data signals and thereby compensate for deviations in the detector responses.

Such prior art methods are disadvantageous for several reasons. In most CT scanners, ring error is not related to projection angle, and therefore, averaging the high frequency signals over several adjacent projection angles does not generate satisfactory offset values. Further, high contrast features in the object being scanned occasionally generate a high frequency signal having a large amplitude, and including such large amplitude high frequency signals in the averaging process generates inaccurate offset values.

There is therefore a need for improved methods and apparatus for reducing rings in CT images.

OBJECTS OF THE INVENTION

It is an object of the present invention to substantially reduce or overcome the above-identified problems of the prior art.

Another object of the invention is to provide a ring suppression filter that generates a histogram signal for each channel describing the error in each channel as a function of the projection amplitude.

Yet another object of the invention is to provide a ring suppression filter which can use global data to suppress rings even in local regions where high quality data indicative of rings is not available.

Still another object of the invention is to provide a computed tomography system that can use data from one or more previous scans to suppress rings in the current scan.

SUMMARY OF THE INVENTION

These and other objects are provided by an improved ring suppression filter for use in a CT system. The system generates projections at a plurality of projection angles, and each projection includes one measurement of each of a plurality of projection data signals. The ring suppression filter includes a high pass filter, a histogram generator, and a combiner. The high pass filter generates a measurement of an error signal corresponding to each of the measurements of one of the projection data signals, and each of the error signal measurements is representative of the high frequency components in a portion of one of the projections. The histogram generator generates a histogram signal representative of a relationship between the measurements of the error signal and the measurements of the one projection data signal. The combiner combines the measurements of the one projection data signal and the histogram signal to generate a plurality of measurements of a ring corrected signal.

The ring suppression filter may generate measurements of a plurality of ring corrected signals, each of the ring corrected signals corresponding to one of the projection data signals. By using the ring corrected signals rather than the projection data signals, the CT system is able to generate CT images having reduced rings.

Still other objects and advantages of the present invention will become readily apparent to those skilled in the art from the following detailed description wherein several embodiments are shown and described, simply by way of illustration of the best mode of the invention. As will be realized, the invention is capable of other and different embodiments, and its several details are capable of modifications in various respects, all without departing from the invention. Accordingly, the drawings and description are to be regarded as illustrative in nature, and not in a restrictive or limiting sense, with the scope of the application being indicated in the claims.

BRIEF DESCRIPTION OF THE DRAWINGS

For a fuller understanding of the nature and objects of the present invention, reference should be had to the following detailed description taken in connection with the accompanying drawings in which the same reference numerals are used to indicate the same or similar parts wherein:

FIG. 7 is a block diagram illustrating a CT system constructed according to the invention which uses data from previous scans to suppress rings in current scans;

FIG. 8 is a block diagram of a signal processing portion of a preferred CT system constructed according to the invention;

FIGS. 11A–B illustrate the spatial relationship between the X-ray source and the detectors for projection angles of zero and 180 degrees, respectively;

FIG. 12 illustrates the spatial relationship between the detector array at projection angles of zero and 180 degrees.

DETAILED DESCRIPTION OF THE DRAWING

Figure 2:
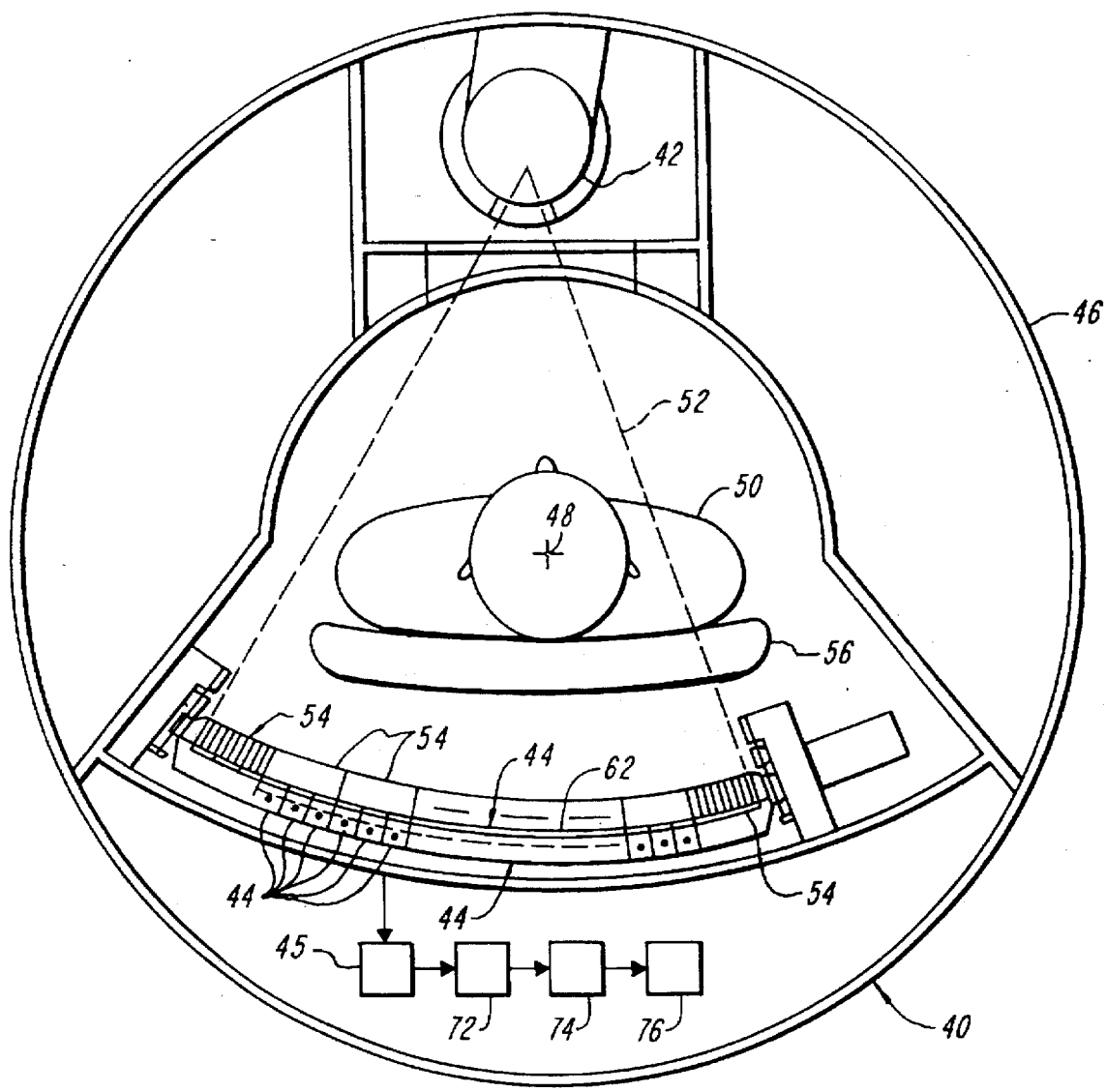
FIG. 2 is an axial view of a preferred CT system constructed according to the invention.

FIG. 2 shows an exemplary CT system, or scanner, 40 incorporating the principles of the present invention. Scanner 40 includes an X-ray source 42 and a detector assembly 44 comprising an array of detectors mounted to a disk 46. Source 42 and detector assembly 44 are rotated about a rotation axis 48 (extending normal to the view shown in FIG. 2) so as to rotate around the object 50 that extends through the central opening of the disk 46 during a CT scan. Object 50 may be a part of a live human patient, such as the head or torso. Source 42 emits within the scanning plane (normal to rotation axis 48) a continuous fan-shaped beam 52 of X-rays, which are sensed by the detectors of assembly 44 after passing through object 50. An array of anti-scatter plates 54 is preferably located between object 50 and the detectors of assembly 44 to substantially prevent scattered rays from being sensed by the detectors. In a preferred embodiment the detectors number 384 and cover an arc of 48°, although the number and angle can vary. Disk 46, which may advantageously be of a light weight material, such as aluminum, is caused to rotate rapidly and smoothly around axis 48. The disk 46 is of an open frame construction so that object 50 can be positioned through the opening of the disk. Object 50 may be supported, for example, on a table 56, which is preferably as transparent as is practical to X-rays.

The output signals generated by the detector assembly 44 are applied to a DAS 70 (shown in block diagram form) which generates therefrom a set of raw data signals. The raw data signals are applied to a projection filter 72 which generates a set of projection data signals. As disk 46 rotates, the projection data signals are used to provide projections from many projection angles. The projection data signals are applied to a ring suppression filter 74 which filters the projection data signals in accordance with the invention in a manner that reduces rings in the reconstructed CT images. The output signals generated by ring suppression filter 74, referred to as "ring corrected projection data signals" or simply as "ring corrected signals", are then applied to a back projector 76 which generates the CT images from the ring corrected signals. The back projector 76 has an input stage that includes a convolution filter for convolving the data as required for back projection.

Scanner 40 is a multi-channel device and the data in each channel transmits one raw data signal, one projection data signal, and one ring corrected signal. In each channel, each of these signals is generated preferably at each of the projection angles.

As will be discussed further below, by using the ring corrected signals generated by ring suppression filter 74 rather than the projection data signals generated by projection filter 72, back projector 76 is able to generate improved CT images having fewer noticeable rings and improved clarity.

As was stated above, a ring is generally caused in reconstructed CT images when one detector is out of calibration with respect to adjacent detectors in the array. Similarly, rings may be caused when any component in a channel causes that channel to be out of calibration with respect to the other channels in the scanner. Further, rings are of course also caused when more than one channel is out of calibration with respect to the other channels. Where a common element or elements are used to process the outputs of each of several subsets of detectors that make up the detector assembly, as for example, where a multiplexor is used to process the detector outputs through such common element or elements, if one of the common elements is out-of-calibration with respect to another then the result will be multiple rings in the final image. Thus, the term "channel" as used herein is the path of a signal that originates from a detector and is then processed through the various described components, with the understanding that several channels may, although not necessarily, share at least a portion of a common signal path, where, for example, those channels share a common element. In any of these events, due to the presence of such deviations in the responses of the channels, the projection data signal(s) in each channel each may be thought of as containing an error component, referred to as a "ring error", superimposed on a data component where each data component is representative of a density of a portion of the patient. Ring suppression filter 74 operates to remove the ring error in each channel so that the ring corrected signals contain only the data components. Thus, CT images reconstructed from the ring corrected signals contain fewer rings and are of improved quality.

Figure 3:
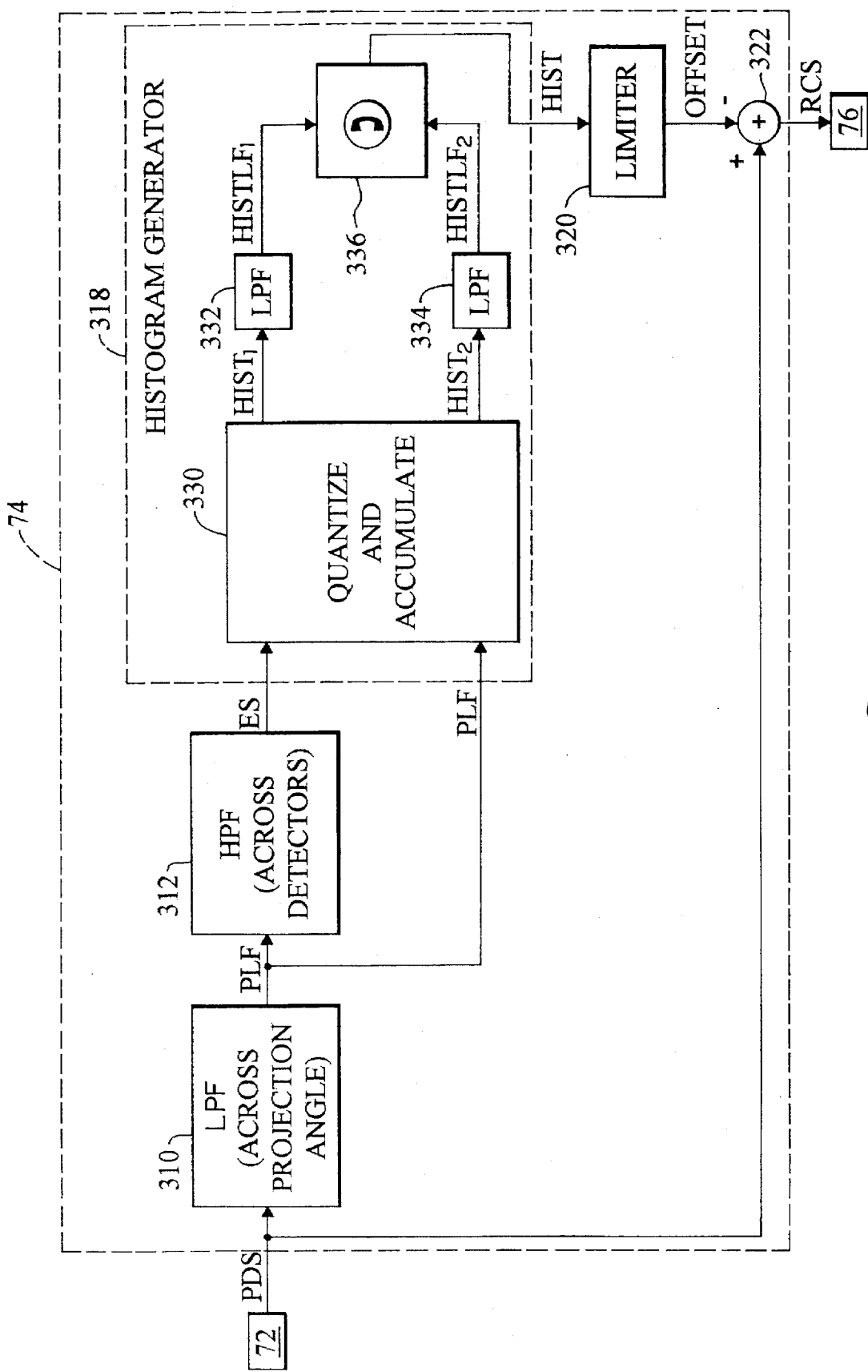
FIG. 3 is a block diagram showing in detail the ring suppression filter shown in FIG. 2.

FIG. 3 shows a block diagram of one embodiment of ring suppression filter 74 constructed according to the invention. Filter 74 receives the projection data signals generated by projection filter 72 and generates therefrom the ring corrected signals that are applied to back projector 76. Ring suppression filter 74 includes a low pass filter 310, a high pass filter 312, a histogram generator 318, a limiter 320, and a subtractor 322. The projection data signals are applied to low pass filter 310 and to a positive input terminal of subtractor 322. Low pass filter 310 filters the projection data signals and thereby generates a set of low frequency projection signals which are applied to high pass filter 312 and to one of two inputs of histogram generator 318. High pass filter 312 filters the low frequency projection signals and thereby generates a set of error signals which are applied to the other input of histogram generator 318. Histogram generator 318 generates a set of histogram signals from the low frequency projection signals and the error signals. The histogram signals are applied to limiter 320 which generates therefrom a set of offset signals that are applied to the negative input terminal of subtractor 322. Subtractor 322 generates the ring corrected signals by subtracting the offset signals from the projection data signals.

The measurements of the projection data signals collected during a single scan (i.e., one rotation of the disk) may be organized in a matrix PDS as shown in the following Equation (1):

$$PDS = \begin{bmatrix} PDS(0,0) & PDS(1,0) & \ldots & PDS(N-1,0) \\ PDS(0,\Delta\theta) & PDS(1,\Delta\theta) & \ldots & PDS(N-1,\Delta\theta) \\ PDS(0,2\Delta\theta) & PDS(1,2\Delta\theta) & \ldots & PDS(N-1,2\Delta\theta) \\ \cdot & & & \\ \cdot & & & \\ PDS(0,360-\Delta\theta) & PDS(1,360-\Delta\theta) & \ldots & PDS(N-1,360-\Delta\theta) \end{bmatrix} \quad (1)$$

Each element $PDS(i,\theta)$ in the PDS matrix represents a measurement of the projection data signal in the ith channel for a projection angle equal to $\theta$. In Equation (1), N represents the number of channels in scanner 40. As stated above, in the preferred embodiment there are 384 detectors in the array 44, so in the preferred embodiment there are 384 channels in scanner 40 and N is equal to 384. As described, the consecutive numbering of the channels from 0 to N−1 corresponds to the same sequencing of the orientation of the detectors, so that numbering the detectors of detector assembly 44 consecutively from one end to the other, channel 0 corresponds to an end detector one, channel 1 corresponds to detector two, positioned between detectors one and three, etc. Δθ represents the amount of rotation of disk 46 between successive projections (i.e., the angular increment of the projection angle between successive projections). In the preferred embodiment, disk 46 rotates one eighth of a degree between each projection and scanner 40 generates 2880 projections in a single scan (i.e., eight projections per degree for 360 degrees), so in the preferred embodiment Δθ is equal to 0.125 degrees. Each row of the PDS matrix represents all the measurements of the projection data signals collected at a single projection angle. In the preferred embodiment, there are therefore 2880 rows in the PDS matrix. Each column of the PDS matrix represents all the measurements (the values of the projection data signal) through one channel collected during one scan, and in the preferred embodiment there are 384 columns in the PDS matrix. Spatially, the PDS matrix has a cyclical nature in which the first row is the continuation of the last row, that is, PDS(i,0)=PDS(i,360) since these two values are taken at the same projection angle, although the values may differ since they may be measured at different times.

Low pass filter 310 preferably generates the low frequency projection signals by low pass filtering the projection data signals across a number of projection angles (i.e., across several rows of the PDS matrix). Low pass filter 310 preferably generates a matrix PLF of measurements of the low frequency projection signals, and each element PLF(i,θ) of the PLF matrix is a measurement of the low frequency projection signal in the ith channel for a projection angle equal to θ. As those skilled in the art will appreciate, the performance of ring suppression filter 74 is not sensitive to the particular form of filter used to implement low pass filter 310, and low pass filter 310 may be implemented using for example finite impulse response (FIR) filters, infinite impulse response (IIR) filters, recursive or non-recursive filters, or by frequency domain filters using for example a Fourier transform technique. In one embodiment, low pass filter 310 generates each element PLF(i,θ) of the PLF matrix so that it is a weighted average of elements of the PDS matrix according to the formula shown in the following Equation (2):

$$PLF(i,\theta) = \frac{\sum_{k=-M}^{M} A_k PDS(i,\theta + k\Delta\theta)}{\sum_{k=-M}^{M} A_k} \quad (2)$$

in which M is preferably equal to 50 (when Δθ is equal to 0.125 degrees) and the weighting factors $A_k$ are all preferably equal to one. Thus, in the preferred embodiment, for a channel i at a projection angle θ, PLF(i,θ) is determined from the PDS values for the projection angle θ, and the previous fifty and the next fifty projection angles, or total angle of about 12.5 degrees. However, other distributions of the weighting factors $A_k$ and other values for M are of course possible. In Equation (2) it is preferable to exploit the cyclical nature of the PDS matrix by interpreting the variable θ as modulo 360 (so that, for example, a value of θ=(360+Δθ) is interpreted as θ=Δθ), so that the data collected at a projection angle of zero degrees "wraps around" to the data collected at 360 degrees.

High pass filter 312 preferably generates the error signals by high pass filtering the low frequency projection signals across several channels (i.e., across several columns of the PLF matrix). Each error signal therefore provides a measure of how different the projection data signal in one channel is from the projection data signals in that channel's neighboring channels. The particular filter used to implement high pass filter 312 is preferably chosen so that each of the error signals provides a good measurement of the ring error in its channel (superimposed of course on a measurement of a data component in its channel, where these data components are representative of the high frequency components of a density profile of the patient).

High pass filter 312 preferably generates a matrix ES of measurements of the error signals, and each element ES(i,θ) of the matrix ES is a measurement of the error signal in the ith channel for a projection angle equal to θ. In one preferred embodiment, high pass filter 312 is implemented as a two pass filter and generates each element ES(i,θ) of the matrix ES according to the formulas shown in Equations (3). The first pass results, PHF(i,θ), are further high pass filtered to generate the second pass results as ES(i,θ). Those skilled in the art will appreciate that these two passes of filtering can be combined into a single pass, and that other forms of high pass filters may also be used, including those that provide more than two passes, use fewer or more neighboring detectors with each pass, those providing different weights to the outputs of neighboring detectors, etc.

$$PHF(i,\theta) = PLF(i,\theta) - \quad (3)$$
$$\tfrac{1}{6}[PLF(i-2,\theta) + 2PLF(i-1,\theta) + 2PLF(i+1,\theta) + PLF(i+2,\theta)]$$
$$ES(i,\theta) = PHF(i,\theta) - \tfrac{1}{5}[PHF(i-2,\theta) +$$
$$PHF(i-1,\theta) + PHF(i,\theta) + PHF(i+1,\theta) + PHF(i+2,\theta)]$$

As can be seen from Equations (3), each high pass filtered signal PHF(i,θ) is determined by the low pass filtered signal for that channel, PLF(i,θ), less the weighted sum of the low pass filtered signals in the next two adjacent channels (detectors) on each side of channel (i), wherein the low pass filtered signals in the two adjacent channels (i−1) and (i+1) are each weighted by a factor of two, the low pass filtered signals in the channels (i−2) and (i+2) on opposite sides of and adjacent to those two channels (detectors) are each weighted by a factor of 1, and the sum of the four signals is divided by six, as can be readily determined, if the value of each of the five low pass filtered signals is the same, the value of PHF(i,θ) is zero indicating there are no differences.

The value of ES(i,θ) is determined with the value of PHF(i,θ) for each channel less the sum of the evenly weighted values of PHF(i−2,θ), PHF(i−1,θ), PHF(i,θ), PHF(i+1,θ) and PHF(i+2,θ) divided by five.

The error signals and the low frequency projection signals are applied to histogram generator 318 which generates therefrom the histogram signals. In the illustrated embodiment, generator 318 includes a quantize and accumulate device 330, two low pass filters 332, 334, and a divider 336. Quantize and accumulate device 330 generates two intermediate signals $HIST_1$, $HIST_2$ for each channel. The $HIST_1$ signals are applied to low pass filter 332 which generates therefrom a set of low pass filtered signals $HISTLF_1$ and the $HIST_2$ signals are applied to low pass filter 334 which generates therefrom a set of low pass filtered signals $HISTLF_2$. Divider 336 receives the filtered signals and generates the histogram signals by dividing the filtered signal $HISTLF_1$ by the filtered signal $HISTLF_2$ in each channel.

Figure 4A:
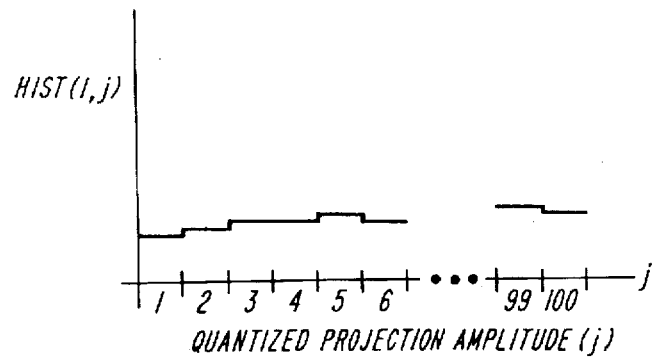
FIG. 4A is a graph showing an example of a histogram signal generated by a ring suppression filter constructed according to the invention.
Figure 4B:
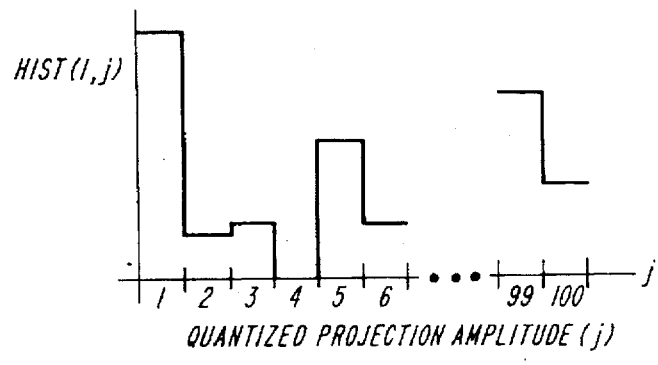
FIGS. 4B–C are graphs of intermediate variables which may be used by a ring suppression filter constructed according to the invention to generate the histogram signals.
Figure 4C:
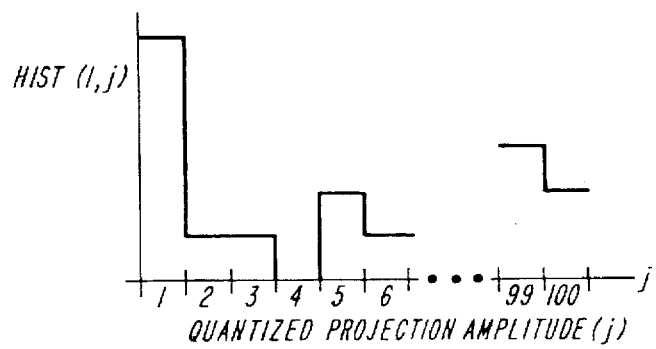

FIGS. 4A, 4B, 4C show graphs illustrating an example of a histogram signal, an intermediate signal $HIST_1$ and an intermediate signal $HIST_2$, respectively, generated by histogram generator 318. Specifically, FIGS. 4A, 4B, and 4C show graphs of a histogram signal HIST(1,j), an intermediate signal $HIST_1(1,j)$, and an intermediate signal $HIST_2(1,j)$, respectively, all for the first channel. While these graphs illustrate signals generated for the first channel, those skilled in the art will appreciate that these graphs are illustrative of signals generated for each of the other channels as well.

In FIGS. 4A–C, the horizontal axis of each graph represents the projection amplitude of the first channel (i.e., the amplitude of the low frequency projection signal in the first channel) which is preferably quantized into several bins. The variable j represents the quantized projection amplitude so that each value of the variable j corresponds to a quantization interval or a range of projection amplitudes. The maximum value of j corresponds to a range that includes the maximum expected value of any of the projection amplitudes, and the minimum value of j corresponds to a range that includes the minimum expected value of any of the projection amplitudes, the difference between the two defining the dynamic range. Histogram generator 318 generates the histogram signals so that they are functions of the quantized variable j. In FIGS. 4A–C, the projection amplitude is shown quantized into one hundred bins corresponding to one hundred intervals, although other numbers of bins may of course be used. In FIG. 4A, the vertical axis represents the ring error in the first channel, so the signal HIST(1,j) shown in FIG. 4A describes the ring error in the first channel as a function of the projection amplitude.

Figure 5:
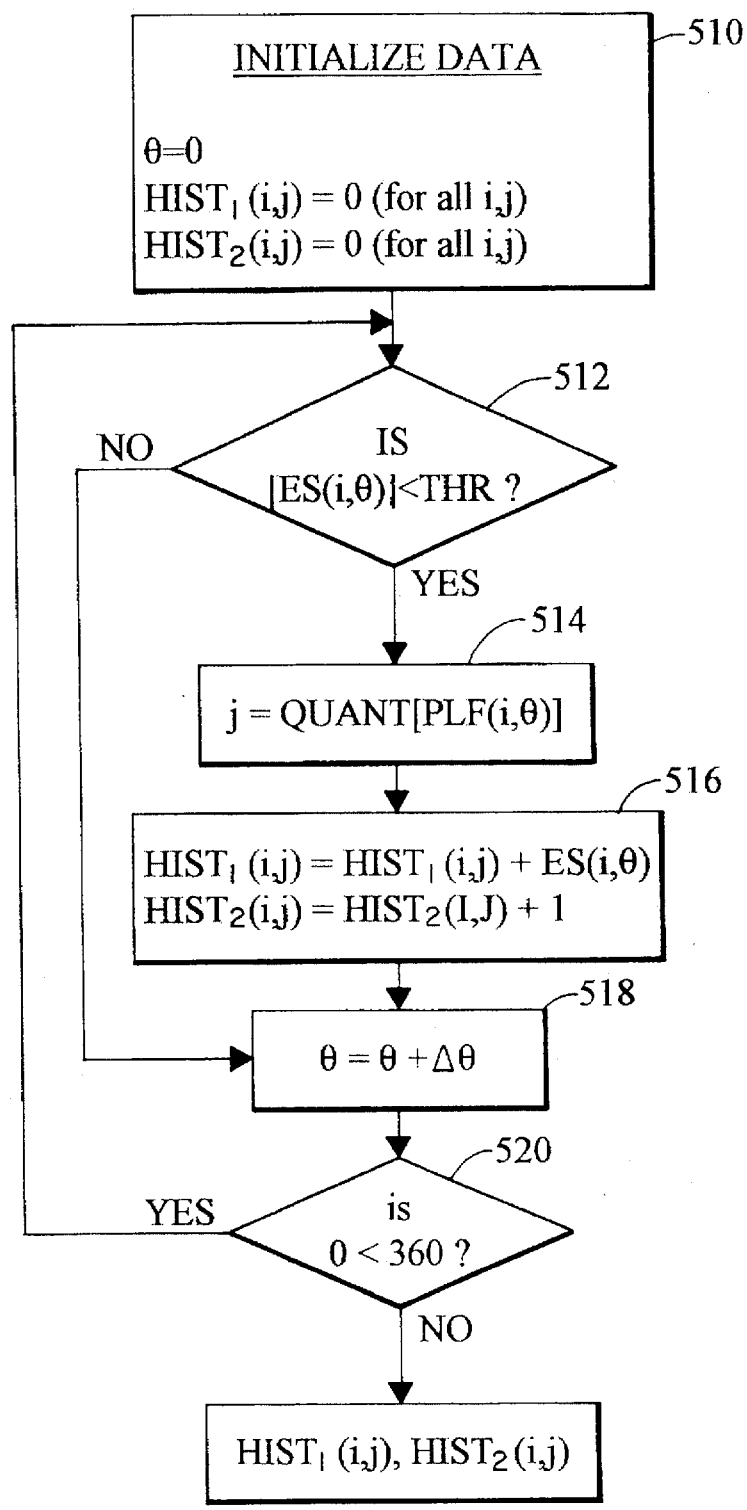
FIG. 5 is a flow chart illustrating a process that a ring suppression filter constructed according to the invention may use to generate the histogram signals.

FIG. 5 is a block diagram illustrating one preferred process 500 which may be used by quantize and accumulate device 330 to generate the intermediate histogram signals $HIST_1$, $HIST_2$ for all the channels. For simplicity, process 500 will be discussed in connection with generating the intermediate histogram signals for the first channel $HIST_1$ (1,j), $HIST_2(1,j)$ although, as those skilled in the art will appreciate, the intermediate histogram signals for the other channels are calculated in a similar manner. The first step in process 500 is an initialization step 510 in which the variables used in the process are set to zero. More specifically, the variable θ, which represents projection angle, is set to zero degrees, and the values of $HIST_1(1,j)$ and $HIST_2(1,j)$ are set to zero for all values of j.

Following step 510, a comparison, or thresholding, step 512 is executed. In step 512 the element ES(1,θ) of the error signal matrix ES is compared to a predetermined threshold value THR. If the absolute value of the element ES(i,θ) is less than the value of THR, then the element ES(i,θ) is said to be "under-threshold", and if the absolute value of element ES(i,θ) is not less than the value of THR, then the element ES(i,θ) is said to be "over-threshold". If the element ES(1,θ) is under-threshold then a quantization step 514, an updating step 516, and an incrementing step 518 will be sequentially executed so that process 500 may use the element ES(1,θ) and the corresponding element PLF(1,θ) of the PLF matrix to generate the intermediate histogram signals. Conversely, if the element ES(1,θ) is over-threshold, then the quantization step 514 and the updating step 516 are skipped, and the incrementing step 518 is next executed so that process 500 will not use the element ES(1,θ) and the corresponding element PLF(1,θ) to generate the histogram signals.

The thresholding step 512 is performed to distinguish between contrasts produced between adjacent detectors due to image data (such as the edge of bone and adjacent soft tissue) in which the absolute value |ES(i,θ)| will be over-threshold, and contrasts due to ring artifacts in which the value of |ES(i,θ)| will be under-threshold. The absolute value of |ES(i,θ)| is empirically determined.

In quantization step 514, a bin number j is preferably calculated by quantizing the element PLF(1,θ) using a quantization function QUANT as shown in Equation (4).

$$j = QUANT[PLF(1,θ)] \tag{4}$$

As those skilled in the art will appreciate, the quantization function QUANT may be implemented many different ways. One preferred quantization function is given by the formula shown in the following Equation (5).

$$QUANT[PLF(i,θ)] = INT\left(\frac{PLF(i,θ)}{\left(\frac{max}{j_{max}}\right)}\right) + 1 \tag{5}$$

In Equation (5), the values max and $j_{max}$ are constants, max is equal to the maximum expected value of the low frequency projection signals, and $j_{max}$ is equal to the maximum value of j (so in an embodiment which generates histogram signals as illustrated in FIGS. 4A–C, j is equal to one hundred). In Equation (5), INT is the well known integer function and in general INT(x) is equal to the integer portion of the argument x (e.g., INT(3.6) is equal to 3).

Once the bin number j has been determined in quantization step 514 then updating step 516 is executed. In updating step 516, the values of $HIST_1(1,j)$ and $HIST_2(1,j)$ are updated. The new value of $HIST_1(1,j)$ is set equal to the old value of $HIST_1(1,j)$ plus the value of the element ES(1,θ), and the new value of $HIST_2(1,j)$ is set equal to the old value of $HIST_2(1,j)$ plus one.

Following updating step 516, incrementing step 518 is executed. In incrementing step 518, the present value of the variable θ is increased by the amount Δθ. Following incrementing step 518, a testing step 520 is executed. In testing step 520, the variable θ is compared to 360 degrees. If θ is less than 360, then step 512, and the subsequent steps, are executed again, and if θ is not less than 360 degrees, then process 500 is complete and the values of $HIST_1(1,j)$ and $HIST_2(1,j)$ have been calculated for one entire scan.

FIGS. 4B and 4C are graphs showing $HIST_1(1,j)$ and $HIST_2(1,j)$, respectively, as calculated by process 500. For each value of j, the value of $HIST_1(1,j)$ is equal to the sum of the elements ES(1,θ) for all values of θ for which ES(1,θ) was under-threshold, and for which QUANT[PLF(1,θ)]was equal to j, and the value of $HIST_2(1,j)$ is equal to the number of elements ES(1,θ) which were summed to form $HIST_1(1, j)$. The intermediate histogram signals, $HIST_1(i,j)$ and $HIST_2(i,j)$, are applied to low pass filters 332, 334, respectively (shown in FIG. 3) which smooths the intermediate signals across a number of projection amplitudes. In one embodiment, low pass filters 332 and 334 generate the filtered histogram signals $HISTLF_1(i,j)$ and $HISTLF_2(i,j)$, respectively according to the formulas shown in the following Equations (6) and (7):

$$HISTLF_1(i,j) = \frac{\sum_{k=-M}^{M} B_k HIST_1(i, j+k)}{\sum_{k=-M}^{M} B_k} \tag{6}$$

$$HISTLF_2(i,j) = \frac{\sum_{k=-M}^{M} B_k HIST_2(i, j+k)}{\sum_{k=-M}^{M} B_k} \tag{7}$$

in which the filtering width M is equal to 8 and the weighting factors $B_k$ are all equal to one, although other distributions of the weighting factors $B_k$ and other values for the filtering width M are of course possible. Further, in other embodiments, other low pass filtering functions may of course be used.

The filtered histogram signals $HISTLF_1(i,j)$ and $HISTLF_2(i,j)$ are then applied to divider 336 shown in FIG. 3. The divider 336 generates the final histogram signals $HIST(i,j)$ for all i and j according to the following Equation (8)

$$HIST(i,j) = \frac{HISTLF_1(i,j)}{HISTLF_2(i,j)} \qquad (8)$$

For each value of j, $HIST(i,j)$ is equal to the average of all the elements $ES(i,\theta)$ which were under-threshold and which had a corresponding projection amplitude lying in bin j. Since each element $ES(i,\theta)$ is representative of a ring error superimposed on a data component, and since the data components tend to cancel each other out when the elements $ES(i,\theta)$ are averaged over a number of projection angles $\theta$ and over several amplitude bins adjacent to j, $HIST(i,j)$ provides a measurement of ring error in the ith channel as a function of projection amplitude.

It is preferable for divider 336 to detect when $HISTLF_2(i,j)$ is equal to zero and to set corresponding values of $HIST(i,j)$ to zero rather than generating an error or overflow condition by attempting to divide by zero. It is even more preferable for divider 336 to increment $HISTLF_2(i,j)$ by one or some other small number prior to preforming the division of Equation (8) to avoid generating erroneous large values for $HIST(i,j)$.

The histogram signals may contain gaps corresponding to projection amplitudes for which no data was available, particularly when the filtering width M used by filters 332, 334 as defined by Equations (6) and (7) is relatively small. For example, the intermediate histogram signals $HIST_1(1,j)$ and $HIST_2(i,j)$ shown in FIGS. 4B–C contain a gap at bin number four (i.e. j=4). Such a gap will occur in the intermediate histogram signals for the ith channel if none of the elements $PLF(i,\theta)$ are quantized into a particular bin, or if all of the elements $PLF(i,\theta)$ which are quantized into a particular bin correspond to elements $ES(i,\theta)$ which are over-threshold. A gap can be as narrow as a single amplitude bin as shown in FIGS. 4B, 4C or as wide as many amplitude bins. Low pass filters 332, 334 tend to fill in such gaps. For example, the gaps shown in FIGS. 4B–C have been filled in so that there is no gap in the histogram signal $HIST(i,j)$ shown in FIG. 4A. While filters 332, 334 tend to fill in relatively narrow gaps they will not completely fill in relatively wide gaps. However, the gaps in the histogram signals do not interfere with the performance of ring suppression filter 74 because a gap in the histogram signals correspond to an absence of projection data at a particular amplitude, and therefore, the gaps would only provide correction for data that does not exist.

It may be preferable for low pass filters 332,334 to use a different method for calculating the filtered histogram signals near the extreme ends of the projection amplitude (e.g., near bin j equal to one). In Equations (6) and (7), the parameter M may be thought of as defining the size of an averaging window used to generate the filtered histogram signals. It may be preferable to reduce the size of the averaging window (for example by decreasing the value of M) when calculating a filtered histogram signal near the extreme ends of the projection amplitude so that the averaging window does not extend beyond either of the extreme ends. So, for example, when calculating $HISTLF_1(i,3)$ and $HISTLF_2(i,3)$ it may be preferable to set M equal to two. Alternatively, the size of the averaging window may be maintained at a constant and the weights $B_k$ may be adjusted so that any values of the histogram signals lying over the extreme ends are ignored (e.g., in Equations (6) and (7) set $B_k$ to zero when j+k is less than one).

It may also be preferable for low pass filters 332, 334 to treat the bin corresponding to the minimum projection amplitude (i.e., j=1) differently from all the other bins. In general, it is preferable to not include this bin in any of the averaging performed by low pass filters 332, 334 so that $HISTLF_1(i,1)$, $HISTLF_2(i,1)$ is set equal to $HIST_1(i,1)$, $HIST_2(i, 1)$, respectively, for all channels i. It is also preferable to not include the values in this bin in any of the averaging performed in the other bins. It is preferable to treat this bin differently because in general, the ring error may behave significantly differently as the projection amplitude approaches zero so the ring error measured for this bin should not be averaged with the ring errors measured in other bins. This bin corresponds to rays in which minimal absorption of X-ray photons has occurred, i.e., rays which pass through only air (and no part of the patient) before becoming incident on an X-ray detector. In most scans, the projection data signals in channels corresponding to detectors near the edge of the detector array are almost always quantized into the minimum amplitude bin (i.e., the patient is almost never disposed between the X-ray source and the detectors near the edge of the array, so the detectors near the edge of the array rarely "see" the patient), and the projection data signals in channels near the center of the detector array are almost never quantized into the minimum amplitude bin (i.e., detectors near the center of the array almost always "see" the patient). So in any given channel, there are typically either many measurements of the error signal for the minimum amplitude bin, or there are none at all. In a channel having many measurements of the error signal for the minimum amplitude bin, there is no need to average these measurements with error signals from other bins; a high quality measurement of the ring error is obtained simply by averaging the large number of measurements of the error signal in the minimum amplitude bin. In a channel having no measurements of the error signal for the minimum amplitude bin, there is no need to estimate the ring error for the minimum amplitude bin.

As was stated above, prior art systems have attempted to measure the ring error by averaging high frequency filtered versions of the projection data signals (i.e., high frequency signals) over several adjacent projection angles. For example, prior art systems have measured the ring error in one channel for a projection angle of 22.5 degrees by averaging the high frequency signals in that channel for all the projection angles between zero and 45 degrees. Such prior art systems are limited because they use "local data" to generate the measurements of ring error. In contrast to such prior art systems, ring suppression filter 74 shown in FIG. 3 and described herein uses "global data" to generate the measurements of the ring error. For each projection amplitude, the histogram signal is generated by averaging the under-threshold error signals from all of the projection angles. This allows filter 74 to correct rings in portions of the image where no good ring correction data is available by using data from other portions of the image, which was not possible in prior art systems.

Moreover, whereas prior art systems generated a single offset measurement for each channel by averaging high frequency signals over adjacent projection angles, filter 74 separates the averaging process into several different bins (of projection amplitude) and thereby obtains a measurement of ring error for each bin. This is useful since the response of a detector may fluctuate as a function of the intensity of the X-rays incident on that detector.

Limiter 320 (shown in FIG. 3) receives the histogram signals from divider 336 and generates therefrom the offset signals. Limiter 320 generates each offset signal so that it is equal to its corresponding histogram signal when the magnitude of histogram signal is less than a threshold, and is limited to the threshold when the magnitude exceeds the threshold. This is useful since the scanned object 50 (shown in FIG. 2) may contain ring like structures which lead to false HIST(i,j) values for the corresponding detector and amplitude. The limiter 320 preferably saturates the histogram signals to an offset limit of MAX_ERR and generates offset signals OFFSET(i,j) according to the following set of Equations (9).

$$OFFSET(i,j) = \begin{cases} MAX\_ERR, & \text{if } HIST(i,j) > MAX\_ERR \\ -MAX\_ERR, & \text{if } HIST(i,j) < -MAX\_ERR \\ HIST(i,j), & \text{otherwise} \end{cases} \quad (9)$$

Those skilled in the art will appreciate that the offset signal OFFSET(i,j) is a form of histogram signal similar to HIST(i,j). The actual value of MAX_ERR used is empirically determined.

The offset signals and the projection data signals are applied to subtractor 322 which generates the ring corrected signals by subtracting the appropriate offset signals from the projection data signals. Subtractor 322 may be thought of as generating a matrix RCS of ring corrected signals, and every element $RCS(i,\theta)$ is generated according to the formula shown the following Equation (10).

$$RCS(i,\theta) = PDS(i,\theta) - OFFSET(i,QUANT[PDS(i,\theta)]) \quad (10)$$

The ring corrected signals are then applied to back projector 76 which generates therefrom the reconstructed CT images. Since each projection data signal may be thought of as containing a data component and a ring error, and since the offset signals are measurements of the ring error, the ring corrected signals contain only the data components. Therefore, by using the ring corrected signals rather than the projection data signals, back projector 76 generates improved reconstructed CT images.

As those skilled in the art will appreciate, there are many different ways to implement ring suppression filter 74. Each of the components of ring suppression filter 74 may be implemented using discrete components, or alternatively, one or more of the components in filter 74 may be implemented on a digital computer such as an array processor. For example, an implementation of subtractor 322 may include a memory, such as a look up table (LUT), which stores a table of offset signals. Such a LUT would be used to generate the ring corrected signals as the projection data signals are received by the subtractor. Further, while filter 74 has been discussed as a digital system, in which each of the signals was sampled (e.g., the projection data signals were sampled to form a matrix PDS) those skilled in the art will appreciate that filter 74 may also be implemented as an analog filter using components which do not sample the signals and rather treat them as continuous signals.

Figure 1:
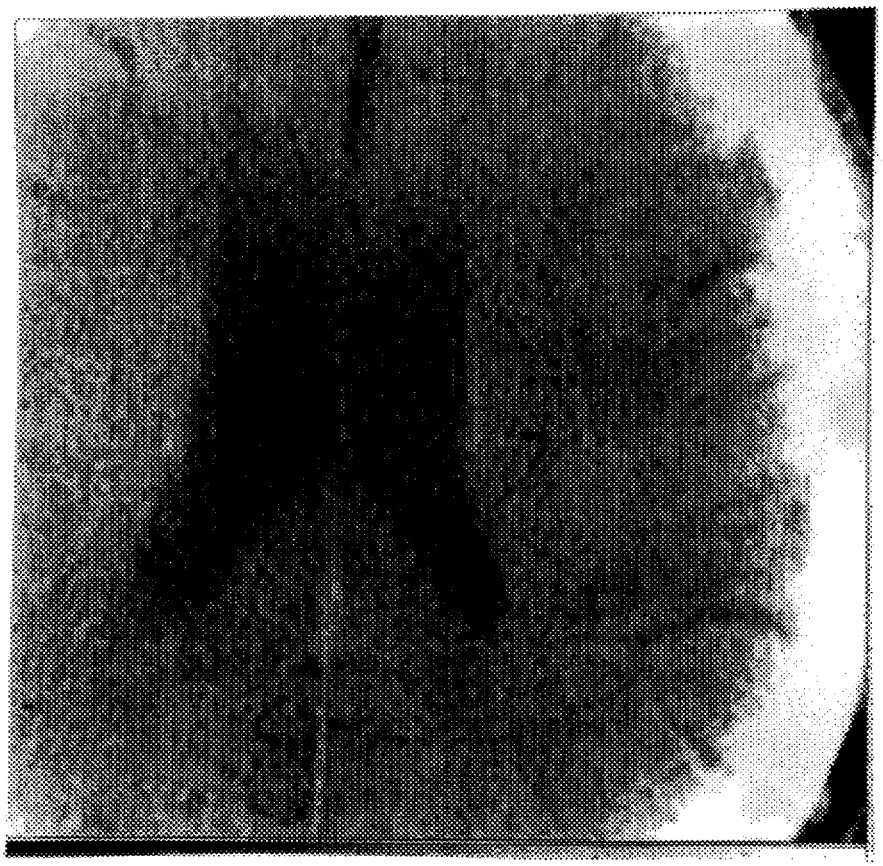
FIG. 1 is a CT image illustrative of the problems associated with rings.
Figure 6:
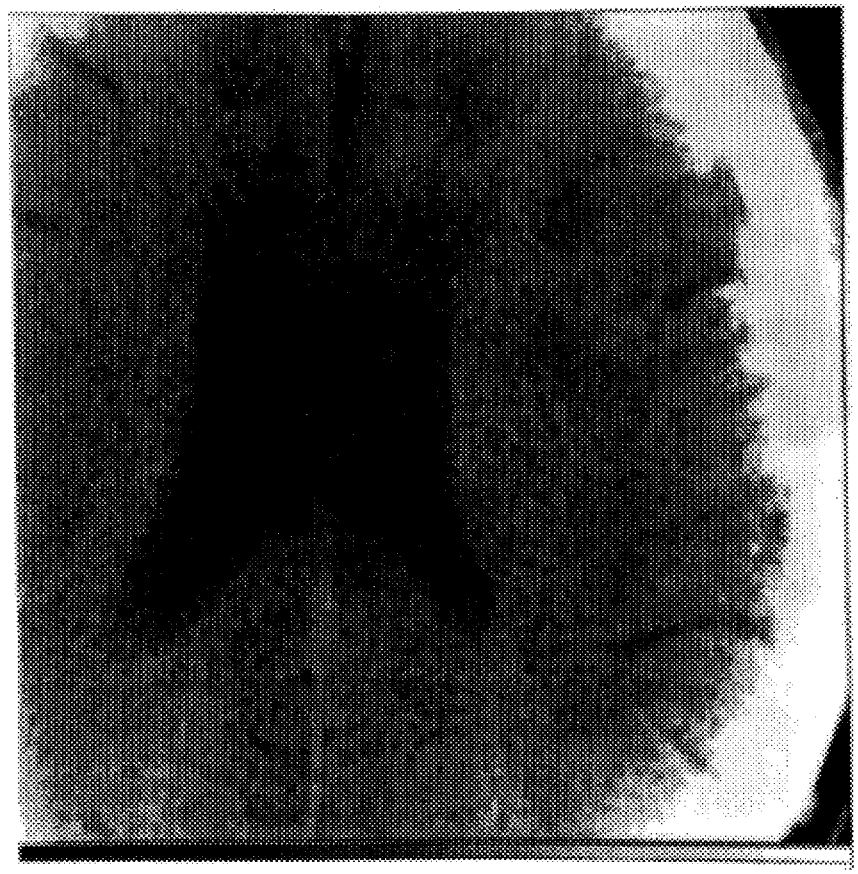
FIG. 6 is an example of a CT image generated by a CT system including a ring suppression filter constructed according to the invention using the same data used to generate the image shown in FIG. 1.

FIG. 6 is a CT image reconstructed using the same data that was used to reconstruct the CT image shown in FIG. 1. However, in FIG. 6, the projection data signals were first processed using ring suppression filter 74. For generation of this image, ring suppression filter 74 used a threshold THR of 0.004 and an offset limit MAX_ERR of 0.002, and the maximum projection amplitude of the patient was typically in the range of 5 to 10. The image shown in FIG. 6 has far fewer noticeable rings than and improved clarity over the image shown in FIG. 1.

Ring suppression filter 74 has been described as generating a set of offset signals from the projection data signals collected in one scan, and using those offset signals to correct the projection data signals (i.e., to generate a set of ring corrected signals) in that same scan. Ring suppression filter 74 may also be used in other modes. For example, it may be preferable to use a set of offset signals generated during one or more previous scans to correct the projection data signals in a current scan. In this mode, the offset signals may be generated "off-line" when the CT system is otherwise idle in which case the speed of ring suppression filter 74 is unimportant. In other modes, ring suppression filter 74 may use projection data signals from one or more previous scans to generate the offset signals. This may be preferable since if any one scan has a shortage of good data for calculating the offset signals (e.g., if an unusually large percentage of the error signals are over-threshold), the other scans may compensate for this shortage. Further, by averaging over several scans, it is possible to generate more accurate offset signals that are less susceptible, for example, to transient phenomena.

In one preferred form, histogram generator 318 generates signals which are weighted averages of previously generated histogram signals from previous scans and ring suppression filter 74 uses these weighted averages to generate the offset signals. In one such form, in the histogram generator 318 of FIG. 3, signals $H\_AVE_1(i,j)$ and $H\_AVE_2(i,j)$ are provided at the outputs of divider 336 and low pass filter 334, respectfully the latter two signals being weighted averages of the histogram signal HIST(i,j) and low pass filtered signal $HISTLF_2(i,j)$, respectively. Initially, $H\_AVE_1(i,j)$ and $H\_AVE_2(i,j)$ are set equal to zero for all values of i and j. After every scan, histogram generator 318 updates a set of weights $W_{old}(i,j)$ and $W_{new}(i,j)$ according to the set of Equations (11), (12) and (13).

$$W_{old}(i,j) = \frac{H\_AVE_2(i,j)}{SUM(i,j)} \quad (11)$$

$$W_{new}(i,j) = \frac{HISTLF_2(i,j)}{SUM(i,j)} \quad (12)$$

$$SUM(i,j) = H\_AVE_2(i,j) + HISTLF_2(i,j) \quad (13)$$

Once the weights $W_{old}(i,j)$ and $W_{new}(i,j)$ have been calculated, the signals $H\_AVE_1(i,j)$ and $H\_AVE_2(i,j)$ are updated according to the formulas shown in the following Equations (14) and (15):

$$H\_AVE_1(i,j) = H\_AVE_1(i,j) * W_{old}(i,j) + HIST(i,j) * W_{new}(i,j) \quad (14)$$

$$H\_AVE_2(i,j) = \begin{cases} H\_AVE_2(i,j) + HISTLF_2(i,j) \\ \text{when}[H\_AVE_2(i,j) + HISTLF_2(i,j)] < T \\ T \text{ otherwise} \end{cases} \quad (15)$$

in which T is a constant threshold. Equations (14) and (15) prevent the signals $H\_AVE_2(i,j)$ from growing larger than T. As those skilled in the art will appreciate, this has the effect of limiting the contributions that older histogram signals from previous scans can make to the signals $H\_AVE_1(i,j)$. Other schemes for limiting the contribution of older histogram signals to the signals $H\_AVE_1(i,j)$ will also function well with the invention.

After every scan, signals HIST(i,j) are generated according to the formula shown in the following Equation (16) (which is identical to Equation (8)) and then the $H\_AVE_1(i,j)$ signals are updated using the signals generated during that scan.

$$HIST(i,j) = \frac{HISTLF_1(i,j)}{HISTLF_2(i,j)} \quad (16)$$

As those skilled in the art will appreciate, the signals H_AVE$_1$(i,j) include weighted averages of past histograms. Once histogram generator 318 generates the signals H_AVE$_1$(i,j), the offset signals may then be generated by applying the H_AVE$_1$(i,j) signals to limiter 320 and the ring corrected signals may then be generated according to Equation (10).

When ring suppression filter 74 uses a history of projection data signals from several scans to generate the ring corrected signals, several modes of operation of filter 74 are possible. In one mode, filter 74 retains the history of ring error information and uses this historical information to generate the offset signals. An example of this mode is for filter 74 to generate the H_AVE$_1$(i,j) signals and to use these signals to generate the offset signals.

FIG. 7 illustrates another mode of operation for filter 74. FIG. 7 is a block diagram of a signal processing portion of a CT system 700 constructed according to the invention. In system 700, projection filter 72 includes a response calibration table 710 and a ring offset table 712. As was stated above, the response calibration table is used to compensate for variations in detector responses, or more precisely the transfer functions of the detectors, and is normally updated infrequently and is generated by scanning "phantoms" in a well known manner. In system 700, the output signals generated by response calibration table 710 are applied to ring offset table 712 which generates therefrom the projection data signals applied to ring suppression filter 74. Ring suppression filter 74 generates the ring corrected signals that are applied to back projector 76, and also updates the contents of the ring offset table 712 via a feedback path. Ring offset table 712 and response calibration table 710 may both be implemented so as to include memories, such as look up tables (LUTs), or as those skilled in the art will appreciate, ring offset table 712 and response calibration table 710 may be combined and implemented as a single LUT.

Initially, following an update of the response calibration table, ring offset table 712 preferably generates the projection data signals so that they are equal to the output signals generated by response calibration table 710. However, after every scan, ring suppression filter 74 updates the contents of ring offset table 712 so the projection data signals are generated using a history of ring error information obtained from prior scans. Ring offset table 712 may be thought of as storing a set of estimates of the ring errors where each estimate is a measurement of the deviation of the response of the corresponding channel from a calibration value since the last update of the response calibration table 710.

So in system 700, projection filter 72 compensates for errors in detector response observed by filter 74 in previous scans, and ring suppression filter 74 compensates for the errors in detector response observed during the current scan. One way to implement system 700 is for ring suppression filter 74 to apply the low pass filtered histogram signals HISTLF$_1$ and HISTLF$_2$ to projection filter 72 so that filter 72 may thereby generate the H_AVE$_1$(i,j) signals and store these signals in table 712. Ring offset table 712 may also include a limiter similar to limiter 320 (shown in FIG. 3) for limiting the value of the H_AVE$_1$(i,j) signals to a threshold such as MAX_ERR. Projection filter 72 then generates the projection data signals according to the following Equation (17)

$$PDS(i,\theta) = PDS_{pre}(i,\theta) - H\_AVE_1(i,QUANT[PDS(i,\theta)]) \quad (17)$$

in which PDS$_{pre}$(i,θ) are measurements of the projection data signals prior to correction by ring offset table 712 (i.e., PDS$_{pre}$(i,θ) are the measurements generated by response calibration table 710).

So in the system 700, the projection data signals generated by filter 72 have been modified to correct for ring errors observed during previous scans by filter 74 (i.e., ring offset table 712 compensates for deviations in channel responses observed between the last update of response calibration table 710 and the most recent scan). Ring suppression filter 74 then corrects the projection data signals for ring errors observed during the current scan by generating the ring corrected signals according to Equation (10). Ring suppression filter 74 also generates a new set of estimates of the ring errors where each of these estimates is a measurement of the deviation of the response of one channel that occurred between the current scan and the most recent previous scan. Projection filter then uses the new estimates from ring suppression filter 74 to update its stored estimates in ring offset table 712.

In any of the modes in which historical information of projection data signals collected during several scans is used to generate the ring corrected signals, the CT system may be thought of as a device for automatically calibrating the transfer functions of the components including the detectors of assembly 44 forming the signal processing channels connected to the input of the ring suppression filter. The CT system still of course generates reconstructed CT images, but in addition to this, the CT system uses data collected while scanning patients to maintain calibration of the detector assembly.

Ring suppression filter 74 has been discussed in connection with use in a CT system for generating the ring corrected signals from the projection data signals supplied by projection filter 72. However, CT systems constructed according to the invention may apply many different types of filtering to the projection data signals prior to reconstructing a CT image. FIG. 8 is a block diagram of the signal processing portion of a preferred CT system 900 constructed according to the invention. System 900, in addition to ring suppression filter 74, includes a parallel beam converter 910, a motion compensation filter 912, a streak suppression filter 914, and an interpolation filter 920. Parallel beam converter 910, motion compensation filter 912 and streak suppression filter 914, as is discussed more fully in the above-referenced U.S. patent application Ser. No. 08/507,468, entitled STREAK SUPPRESSION FILTER FOR USE IN COMPUTED TOMOGRAPHY SYSTEMS and U.S. patent application Ser. No. 08/614,623, entitled MOTION ARTIFACT SUPPRESSION FILTER FOR USE IN COMPUTED TOMOGRAPHY SYSTEMS, both applications being incorporated by reference, are used to suppress other types of artifacts from the CT images. In one preferred embodiment of system 900, the projection data signals generated by projection filter 72 are applied to parallel beam converter 910 which generates therefrom a set of parallel beam signals. The parallel beam signals are applied to ring suppression filter 74 which generates the ring corrected signals. The ring corrected signals are applied to motion compensation filter 912 which generates a set of motion-compensated signals. The motion-compensated signals are then applied to streak suppression filter 914 which generates therefrom a set of streak-suppressed signals. The streak-suppressed signals are then applied to interpolation filter 920, the output of which is applied to back projector 76 which generates therefrom the reconstructed CT images.

In other embodiments of system 900, any one, two, or three of the parallel beam, ring suppression, motion compensation, and streak suppression filters may be eliminated. However, the preferred embodiment of system 900 includes all four filters 910, 74, 912, 914. In other embodiments, ring suppression filter 74 may of course be coupled to projection filter 72 via a feedback path as was discussed in connection with FIG. 7. In still other embodiments, ring suppression filter 74 and/or streak suppression filter 914 may be coupled between projection filter 72 and parallel beam converter 910 rather than between parallel beam converter 910 and back projector 76.

Parallel beam converter 910 includes a reorder converter 916 and an interleave converter 918. Reorder converter 916 receives the projection data signals from projection filter 72 and generates therefrom a set of reordered signals. The reordered signals are applied to interleave converter 918 which generates therefrom the parallel beam signals. The projections generated by projection filter 72 may be thought of as "fan beam" data, since all the projections are generated using fan beam 52 (shown in FIG. 2). Parallel beam converter 910 re-organizes the projections to form parallel beam projections.

Figure 9A:
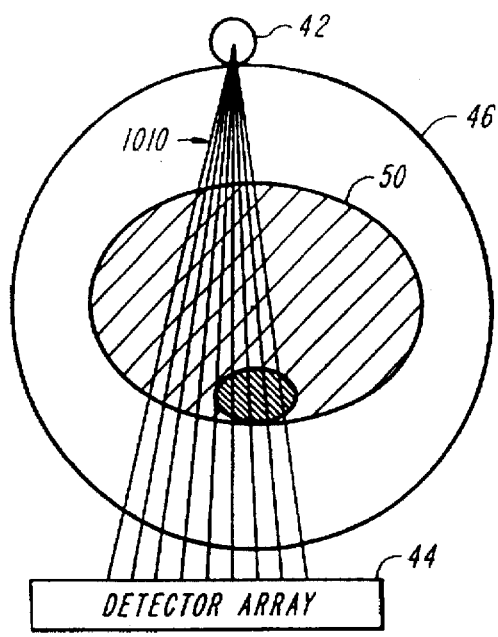
FIGS. 9A–B illustrate generation of fan beam and parallel beam projections, respectively.
Figure 9B:
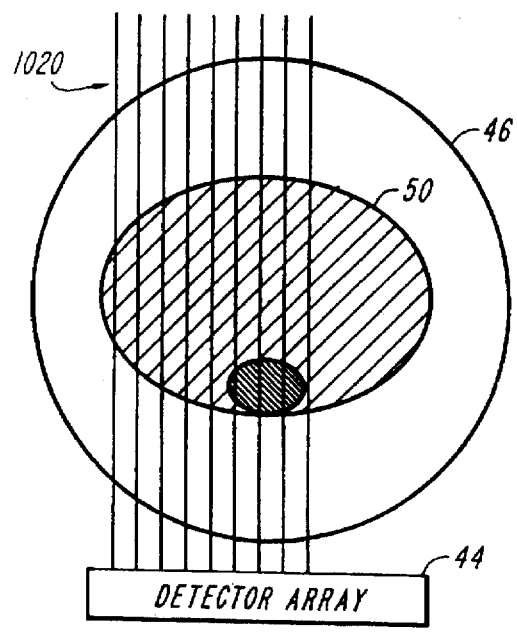

FIG. 9A illustrates a set of rays 1010 forming one portion of a single projection view of a cross section of patient 50. Since each of the rays emanates from X-ray source 42, which is essentially a point source, none of the rays 1010 are parallel, and the resulting projection is a fan beam projection. Each row of the PDS matrix corresponds to a single fan beam projection. Reorder converter 916 re-organizes the projection data signals so that each re-organized projection is formed by a set of parallel rays such as the rays 1020 shown in FIG. 9B.

Figure 10A:
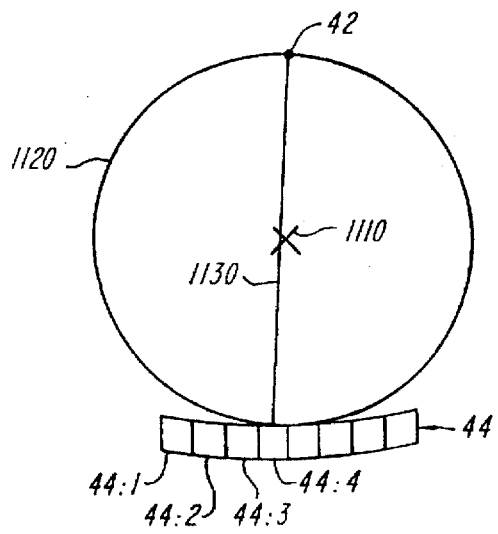
FIGS. 10A–B illustrate one method which may be used by CT systems constructed according to the invention to generate parallel beam projections.
Figure 10B:
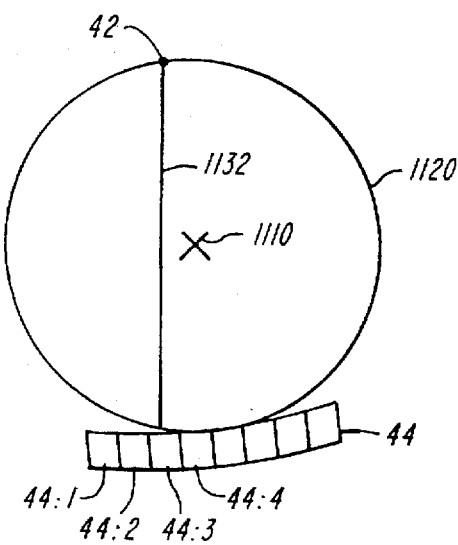

FIGS. 10A–B illustrate one preferred method, which may be used by reorder converter 916, for generating the re-organized projections. FIGS. 10A–B show the positions of X-ray source 42 and detector array 44 during generation of two successive projection views. During a scan, X-ray source 42 and detector array 44 rotate in a counter clockwise direction about a center 1110 of circle 1120. During the first projection, shown in FIG. 10A, a ray 1130 is incident on a detector 44:4 (i.e., the detector of array 44 forming a part of the fourth channel). During the next projection, shown in FIG. 10B, a ray 1132 is incident on detector 44:3 (i.e., the detector of array 44 forming a part of the third channel). In the preferred embodiment, the spacing between the detectors is matched to the amount of rotation between generation of successive projections so that ray 1130 is parallel to, and slightly offset from, ray 1132. In the preferred embodiment, this basic relationship is true for all detectors so that any two rays incident on adjacent detectors during successive projections are parallel and are slightly offset from each other. As was stated above, in the preferred embodiment Δθ is equal to 0.125 degrees, so in the preferred embodiment, each detector in array 44 is spaced apart from its adjacent detectors by 0.125 degrees. Reorder converter 916 uses this basic relationship to reorder the data and generate the re-organized projections.

Reorder converter 916 preferably re-organizes the PDS matrix to form a matrix RE of reordered signals so that each row of the RE matrix is equivalent to a projection formed by a parallel beam. Reorder converter 916 preferably generates the RE matrix so that each element RE(i,θ) of the RE matrix is chosen according to the formula shown in the following Equation (18).

$$RE(i,\theta) = PDS(i,[i-k][\Delta\theta]+\theta) \quad (18)$$

where the kth channel is the channel nearest to the geometrical center of the detector array. Each element RE(i,θ) of the RE matrix represents a measurement of the reordered signal in the ith channel for a parallel beam projection angle of θ.

Reorder converter 916 may also include a low pass filter to average the projections of adjacent projection angles for each channel. The averaged, or decimated, parallel beam matrix RE(i,θ) will have fewer numbers of rows spaced at a larger angular interval Δθ. Decimating the RE matrix in this fashion may be preferable since it reduces the computations for subsequent operations.

Interleave converter 918 (shown in FIG. 8) receives the reordered signals and generates therefrom the parallel beam signals. Interleave converter 918 preferably combines pairs of parallel beam projections that are spaced apart by 180 degrees to form denser projections. FIGS. 11A and 11B illustrate the spatial relationship between X-ray source 42, a cross section of patient 50, and detector array 44 for projection angles of zero and 180 degrees, respectively. In FIGS. 11A–B, detector array 44 is shown containing seven detectors, and the detector forming a part of the fourth channel 44:4 is the central detector of the array 44. As was stated above, in the preferred embodiment, detector array 44 has 384 detectors, however, for ease of illustration, a seven detector embodiment will now be discussed. In the preferred embodiment, detector array 44 is slightly offset from the center 1210 of disk 46 such that a line 1234 intersecting the focal spot of source 42 and center 1210 does not intersect the center of the central detector 44:4. The arrangement of such a detector system is more fully described in U.S. patent application Ser. No. 08/191,428, entitled, X-RAY TOMOGRAPHY SYSTEM FOR AND METHOD OF IMPROVING THE QUALITY OF A SCANNED IMAGE, filed on Feb. 3, 1994, (Attorney Docket No. ANA-044) and assigned to the present assignee, which is hereby incorporated by reference.

FIG. 12 illustrates the spatial relationship between detector array 44 at projection angles of zero and 180 degrees, and the rays 1310, 1312, 1314 incident on three of the detectors. Because of the offset between array 44 and the center 1210 of disk 46, the detector array 44 at a projection angle of zero degrees is slightly offset from the detector array 44 at 180 degrees. Consequently, the ray 1310 that is incident on the sixth channel detector 44:6 for a projection angle of 180 degrees falls between the rays 1312 and 1314 that are incident on detectors 44:2 and 44:3, respectively, for a projection angle of zero degrees. In this example, detector 44:6 may be thought of as a "central" detector and detectors 44:2 and 44:3 may be thought of as "opposite-adjacent" detectors. At each projection angle, each detector measures the density of a portion of the patient, and in general, the portions measured by the opposite-adjacent detectors are closer to the portion measured by the central detector than are the portions measured by any other detectors (e.g., the portions measured by detectors 44:2, 44:3 at a projection angle of zero degrees are closer to the portion measured by detector 44:6 at a projection angle of 180 degrees than are the portions measured by detectors 44:5, 44:7 at a projection angle of 180 degrees). Any two projections separated by 180 degrees may be interleaved using this relationship between central and opposite-adjacent detectors to form a single denser projection. For example, one such interleaved projection for the arrangement shown in FIG. 12 is composed of the quantities [RE(1,0), RE(7,180), RE(2,0), RE(6,180), RE(3,0), RE(5,180), RE(4,0), RE(4,180), RE(5,0), RE(3,180), RE(6,0), RE(2,180), RE(7,0), RE(1,180)]in which RE(i,θ) is the reordered signal generated from the detector in the ith channel at a projection angle of θ. Interleave converter 918 interleaves the reordered signals in this manner to form denser projections.

Interleave converter 918 preferably generates a matrix PAR of measurements of the parallel beam signals, and each element PAR(i,θ) of the PAR matrix is a measurement of the parallel beam signal in the ith channel for a parallel beam projection angle equal to θ. The structure of the PAR matrix is shown in the following Equation (19):

$$PAR = \begin{bmatrix} PAR(0,0) & PAR(1,0) & \ldots & PAR(2N-1,0) \\ PAR(0,\Delta\theta) & PAR(1,\Delta\theta) & \ldots & PAR(2N-1,\Delta\theta) \\ PAR(0,2\Delta\theta) & PAR(1,2\Delta\theta) & \ldots & PAR(2N-1,2\Delta\theta) \\ \vdots & & & \\ PAR(0,180-\Delta\theta) & PAR(1,180-\Delta\theta) & \ldots & PAR(2N-1,180-\Delta\theta) \end{bmatrix} \quad (19)$$

As shown in Equation (19), the PAR matrix has twice as many columns as the PDS matrix, and half as many rows. So each row of the PAR matrix represents a parallel beam projection containing twice as much data as a row of the PDS matrix. So, each parallel beam projection may be thought of as having image data from twice as many channels as a fan beam projection. Slightly different from the PDS matrix, the PAR matrix has a cyclical property in which the last row continues into the first row in reverse order, so that, PAR(0,180)=PAR(2N−1,0); PAR(1,180)= PAR(2N−2,0), and so on. In the preferred embodiment, interleave converter 918 generates the elements of the PAR matrix according to the formula shown in the following set of Equations (20):

$$PAR(2i,\theta) = RE(i,\theta) \quad (20)$$
$$PAR(2i+1,\theta) = RE(N-1-i,\theta+180)$$
for $0 \leq i < N$ As is well known, parallel beam converters such as converter 910 (shown in FIG. 8) for converting fan beam data to parallel beam data normally include an interpolation filter, such as filter 920 (shown in FIG. 8). However, the interpolation filter is normally disposed immediately following the interleave converter 918. Since the detectors are generally spaced so that the angular offset between adjacent detectors, relative to the X-ray source, is equal for all detectors, the detectors are not spaced equidistantly in a linear sense. Therefore, each row of the PAR matrix (i.e., each parallel beam projection) contains data points which are not spaced equidistantly. Rather, the elements near the middle of each projection, i.e., near the center ray passing through the isocenter, are spaced further apart than are elements near the ends of each projection. The interpolation filter interpolates the data and generates a new matrix of parallel beam data such that all the elements of each projection are spaced equidistantly. In the preferred embodiment, the interpolation filter 920 uses known techniques to interpolate the data and generate projections containing equidistantly spaced elements, however, filter 920 is preferably disposed after streak compensation filter 914 as shown in FIG. 8, rather than immediately following the interleave converter 918. However, the invention will also function well if the interpolation filter 920 is disposed immediately following the interleave converter 918 as is normally done in the prior art.

Also, as is well known, converting fan beam data to parallel beam data generally introduces a slight rotation such that the parallel beam projection angle of zero degrees is not exactly coincident with the fan beam projection angle of zero degrees. If not corrected, this rotation results in generating a reconstructed image that is slightly rotated from the horizontal. This rotation is generally introduced because the center detector 'k' as used in Equation (18) is generally not exactly centered on a line passing from the source through the isocenter to the center detector 'k'. The amount of rotation is generally smaller than Δθ/2 and may be corrected using well known techniques by either the interpolation filter 920 or by the back-projector 76 or alternatively may simply be ignored.

Figure 13:
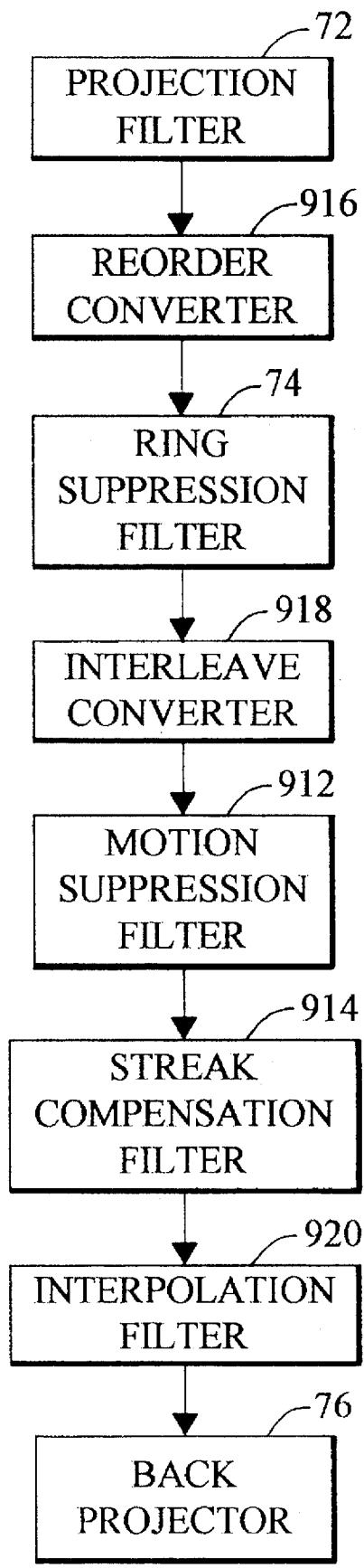
FIG. 13 shows a block diagram of a signal processing portion of another preferred CT system constructed according to the invention.

So, in the embodiment illustrated in FIG. 8, ring suppression filter 74 operates on the parallel beam data generated by parallel beam converter 910. Due to the possible presence of motion artifacts in the data, it may actually be preferable for ring suppression filter 74 to generate the parallel beam histogram and offset signals as functions of the non-interleaved signals (i.e., using the reordered signals generated by reorder converter 916). FIG. 13 shows a block diagram of the signal processing portion of another preferred CT system 1300 constructed according to the invention. System 1300 is similar to system 900 (shown in FIG. 8), however, in system 1300, ring suppression filter 74 is coupled between reorder converter 916 and interleave converter 918 rather than between interleave converter 918 and motion suppression filter 912. In this embodiment, ring suppression filter 74 operates substantially as described above except ring suppression filter 74 operates on the reordered signals generated by reorder filter 916 rather than the projection data signals generated by projection filter 72.

Since certain changes may be made in the above apparatus without departing from the scope of the invention herein involved, it is intended that all matter contained in the above description or shown in the accompanying drawing shall be interpreted in an illustrative and not a limiting sense.

What is claimed is:

1. A computed tomography system for creating a computed tomographic image of a patient and including (a) a source of X-rays and (b) channel defining means for defining a plurality of signal processing channels having corresponding transfer functions and comprising means, including a corresponding plurality of detectors of a detector array for detecting X-rays emitted from said source, for generating a plurality of image data signals as a function of the X-rays detected by the corresponding detectors at each of a plurality of projection angles of a tomographic scan and representative of the tomographic image of the patient, said system further comprising:

means for generating error correction data in response to image data signals generated during an entire scan of a patient; and means for automatically calibrating the transfer functions of said channels as a function of said error correction data so as to minimize ring artifacts in computed tomographic images produced from said image data signals.

2. A computed tomography system for creating a computed tomographic image of a patient and including (a) a source of X-rays and (b) channel defining means for defining a plurality of signal processing channels having corresponding transfer functions and comprising means, including a corresponding plurality of detectors of a detector array for detecting X-rays emitted from said source, for generating a plurality of image data signals as a function of the X-rays detected by the corresponding detectors at each of a plurality of projection angles of a tomographic scan and representative of the tomographic image of the patient, said system further comprising:

means for automatically calibrating the transfer functions of said channels as a function of error correction data obtained from image data signals generated during a scan of a patient so as to minimize ring artifacts in computed tomographic images produced from said image data signals, said means for automatically calibrating the transfer functions of said channels including means for determining the error correction data from each of said image data signals processed through each channel as a function of the amplitude of the data signals processed through that channel.

3. A computed tomography system according to claim 2, wherein said means for determining error correction data from each of said image data signals processed through each channel as a function of the amplitude of the data signals processed through that channel includes means for generating an estimate signal representative of the estimated error in the transfer function for each of said channels at each of said projection angles, means for comparing the value of the amplitude of each of said estimate signals with a predetermined threshold value, and means for generating error correction data for each of said estimate signals only when the value of the estimate signal is under-threshold.

4. A computed tomography system according to claim 1, wherein said means for automatically calibrating the transfer function of said channels includes means for determining error correction data from each of said image data signals processed through each channel as a function of the amplitude of the data signals provided by the corresponding detector and processed through that channel and the amplitudes of the data signals processed through channels associated with detectors of said array adjacent to the corresponding detector.

5. A computed tomography system according to claim 1, wherein said means for automatically calibrating the transfer function of said channels includes means for determining error correction data from each of said image data signals processed through each channel as a function of the amplitude of the data signals provided by the corresponding detector and processed through that channel and the amplitudes of the data signals processed through channels associated with detectors of said array adjacent to the corresponding detectors for preselected ones of said projection angles.

6. A computed tomography system according to claim 1, wherein said means for automatically calibrating the transfer functions of said channels includes means for determining error correction data from each of said image data signals processed through each channel as a function of the amplitude of the data signals provided by the corresponding detector and processed through that channel for each of a predetermined number of projection angles.

7. A computed tomography system according to claim 1, wherein said means for automatically calibrating the transfer functions of said channels includes means for determining error correction data from each of said image data signals processed through each channel as a function of (a) the amplitude of the data signals provided by the corresponding detector and processed through that channel at each of said projection angles, and (b) the amplitude of the data signals of that detector at a preselected number of adjacent projection angles.

8. A computed tomography system according to claim 7, wherein said means for automatically calibrating the transfer functions of said channels includes means for determining error correction data from each of said image data signals processed through each channel as a function of the amplitude of the data signals provided by the corresponding detector and processed through that channel and the amplitudes of the data signals processed through channels associated with detectors of said array adjacent the corresponding detector.

9. A computed tomography system for scanning an object comprising:
(a) a plurality of signal processing means, including a corresponding plurality of detectors, for generating a respective plurality of projection data signals at a plurality of projection angles, each of the signal processing means being characterized by a respective one of a plurality of transfer functions, each of the projection data signals including a data component and an error component, the error components being representative of relative differences between the transfer functions of the signal processing means and also being representative of variations in the transfer functions independent of each other and occurring over time, the data components being representative of the densities of portions of the object, and
(b) a filter comprising means for generating a plurality of estimates of the error components for each of said detectors, each of the estimates being a function of the average amplitude of a predetermined number of the projection data signals acquired by the corresponding detector at a predetermined number of projection angles.

10. A computed tomography system according to claim 9, further comprising means for correcting the error components in each of the projection data signals independent of the other projection data signals.

11. A computed tomography system according to claim 9, wherein said filter includes a filter kernel which is constant for all detectors at all of the projection angles.

12. A computed tomography system according to claim 9, wherein said filter in a non-linear filter.

13. A computed tomography system according to claim 12, wherein said non-linear filter includes (a) threshold means for comparing each measurement of the projection data signals to a threshold and for designating each measurement of the projection data signal that is less than the threshold as being under-threshold, and (b) histogram means for averaging all the measurements of the measurement error signal that correspond to under-threshold measurements of the projection data signal.

14. A computed tomography system for generating a computed tomographic image of an object, the system including means for generating a plurality of projections, each of the projections being generated at a corresponding projection angle, each of the projections including a measurement of each of a plurality of projection data signals, each of the measurements of the projection data signals being representative of a density of a portion of the object, said system further including a ring suppression filter for suppressing ring artifacts in the tomographic image, said filter comprising:
(A) high pass filter means for generating a plurality of measurement error signals as a function of the corresponding measurements of the projection data signals for each of said projections, each measurement error signal being representative of a high frequency component associated with at least a portion of one of the projections;
(B) threshold means for comparing each of the measurements of the projection data signals to a threshold and for designating each measurement of the projection data signal that is less than the threshold as being under-threshold; and (C) histogram means for averaging all the measurements of the measurement error signal that correspond to under-threshold measurements of the projection data signal.

15. In a computed tomography system for generating an image of an object, said system including means for generating a plurality of projections, each of the projections being generated at a corresponding projection angle, each of the projections including one measurement of each of a plurality of projection data signals, each of the measurements of the projection data signals being representative of a density of a portion of the object, a ring suppression filter comprising:

(A) high pass filter means for generating a plurality of measurements of an error signal, each of the measurements of the error signal being representative of the high frequency components associated with a portion of one of the projections;

(B) histogram means, responsive to the measurements of one of the projection data signals and to the measurements of the error signal, for generating a histogram signal, the histogram signal being representative of a relationship between the select measurements of the error signal and each of the corresponding projection data signals; and (C) combining means, responsive to the measurements of the corresponding projection data signal and to the histogram signal, for generating therefrom a plurality of measurements of a ring corrected signal.

16. A ring suppression filter according to claim 15, wherein the histogram means includes quantization means for assigning one of a plurality of bin numbers to each of the measurements of the one projection data signal and the error signal so that each measurement of the one projection data signal and a corresponding measurement of the error signal are assigned the same bin number.

17. A ring suppression filter according to claim 16, wherein the quantization means assigns the same bin number to measurements of the one projection data signal having the same amplitude.

18. A ring suppression filter according to claim 17, wherein the histogram means generates the histogram signal so that the histogram signal has a value for each of the bin numbers.

19. A ring suppression filter according to claim 18, wherein the histogram means averages all the measurements of the error signal that are assigned to one bin number to generate the value of the histogram signal for that one bin number.

20. A ring suppression filter according to claim 18, wherein the histogram means averages all the measurements of the error signal that are assigned to one bin number and that have a magnitude less than a threshold to generate the value of the histogram signal for that one bin number.

21. A ring suppression filter according to claim 18, wherein the histogram means includes means for comparing each of the measurements of the error signal to a threshold and further includes means for designating each of the measurements of the error signal having a magnitude less than the threshold as an under-threshold measurement.

22. A ring suppression filter according to claim 21, wherein the histogram means averages all the under-threshold measurements that are assigned to one bin number to generate the value of the histogram signal for that one bin number.

23. A ring suppression filter according to claim 22, wherein the combining means generates each measurement of the ring corrected signal by determining which bin number has been assigned to one of the measurements of the one projection data signal and then subtracting from the one measurement of the one projection data signal the value of the histogram signal for that bin number.

24. A ring suppression filter according to claim 21, wherein the histogram means includes means for generating a first intermediate signal and a second intermediate signal, for each bin number the first intermediate signal having a value substantially equal to a sum of all the under-threshold measurements of the error signal assigned to that bin number, and for each bin number the second intermediate signal having a value substantially equal to a total number of all the under-threshold measurements of the error signal assigned to that bin number.

25. A ring suppression filter according to claim 21, wherein the histogram means includes first low pass filter means for receiving and low pass filtering the first intermediate signal and thereby generating a first filtered signal, and wherein the histogram means includes second low pass filter means for receiving and low pass filtering the second intermediate signal and thereby generating a second filtered signal.

26. A ring suppression filter according to claim 25, wherein the histogram means includes dividing means for dividing the first intermediate signal by the second intermediate signal and thereby generating the histogram signal.

27. A ring suppression filter according to claim 26, further including offset means for receiving the histogram signal and for generating therefrom an offset signal, the offset signal having a magnitude less than or equal to that of the histogram signal.

28. A ring suppression filter according to claim 15, further including low pass filter means for low pass filtering the each of the projections and for applying the low pass filtered projections to the high pass filter means.

29. A ring suppression filter according to claim 15, wherein each of the projections is a fan beam projection.

30. A ring suppression filter according to claim 15, wherein each of the projections is a parallel beam projection.

31. A ring suppression filter according to claim 15, wherein said histogram means is responsive to measurements of projection data signals and error signals generated during two or more scans.

32. A computed tomography system for creating a tomographic image of a scanned object and including a source of X-rays and channel defining means for defining a plurality of signal processing channels characterized by a corresponding plurality of transfer functions, said plurality of signal processing channels comprising means, including a corresponding plurality of detectors of a detector array for detecting X-rays emitted from said source, for generating a plurality of data signals as a function of the X-rays detected by the corresponding detectors at each of a plurality of projection angles of a tomographic scan through the corresponding signal processing channels, said system further including:

means for automatically calibrating the transfer functions of said channels as a function of error correction data obtained from data signals generated during at least one previous scan of a patient so as to minimize ring artifacts in tomographic images produced from said data signals.

33. A computed tomography system according to claim 32, wherein said means for automatically calibrating the transfer functions of said channels as a function of error correction data obtained from data signals generated during at least one previous scan of a patient and the present scan of a patient so as to minimize ring artifacts in tomographic images produced from said data signals.

34. A computed tomography system according to claim 32, wherein said means for automatically calibrating the transfer functions of said channels as a function of error correction data obtained from data signals generated during a plurality of previous scans of one or more patients so as to minimize ring artifacts in tomographic images produced from said data signals.

35. A computed tomography system according to claim 32, wherein said means for automatically calibrating the transfer functions of said channels includes means for determining the error correction data from each of said image data signals processed through each channel as a function of the amplitude of the data signals processed through that channel.

36. A computed tomography system according to claim 32, wherein said means for determining error correction data from each of said image data signals processed through each channel as a function of the amplitude of the data signals processed through that channel, means for generating an estimate signal representative of the estimated error in the transfer function for each of said channels at each of said projection angles, means for comparing the value of the amplitude of each of said estimate signals with a predetermined threshold value, and means for generating error correction data for each of said estimate signals only when the value of the estimate signal is under-threshold.

37. A computed tomography system according to claim 32, wherein said means for automatically calibrating the transfer function of said channels includes means for determining error correction data from each of said image data signals processed through each channel as a function of the amplitude of the data signals provided by the corresponding detector and processed through that channel and the amplitudes of the data signals processed through channels associated with detectors of said array adjacent to the corresponding detector.

38. A computed tomography system according to claim 32, wherein said means for automatically calibrating the transfer function of said channels includes means for determining error correction data from each of said image dam signals processed through each channel as a function of the amplitude of the data signals provided by the corresponding detector and processed through that channel and the amplitudes of the data signals processed through channels associated with detectors of said array adjacent to the corresponding detectors for preselected ones of said projection angles.

39. A computed tomography system according to claim 32, wherein said means for automatically calibrating the transfer functions of said channels includes means for determining error correction data from each of said image data signals processed through each channel as a function of the amplitude of the data signals provided by the corresponding detector and processed through that channel for each of a predetermined number of projection angles.

40. A computed tomography system according to claim 32, wherein said means for automatically calibrating the transfer functions of said channels includes means for determining error correction data from each of said image data signals processed through each channel as a function of (a) the amplitude of the data signals provided by the corresponding detector and processed through that channel at each of said projection angles, and (b) the amplitude of the data signals of that detector at a preselected number of adjacent projection angles.

41. A computed tomography system according to claim 40, wherein said means for automatically calibrating the transfer functions of said channels includes means for determining error correction data from each of said image data signals processed through each channel as a function of the amplitude of the data signals provided by the corresponding detector and processed through that channel and the amplitudes of the data signals processed through channels associated with detectors of said array adjacent the corresponding detector.

42. A computed tomography system for scanning objects through a plurality of projection angles, the system including a plurality of signal processing means including respectively a plurality of detectors of a detector array, each of the processing means for generating a respective one of a plurality of projection data signals and each of the processing means being characterized by a respective one of a plurality of signal transfer functions, each of the projection data signals including a data component and an error component, the error components being representative of relative differences between the signal transfer functions of the processing means, the plurality of processing means generating their respective projection data signals for each scan so that the data components are representative of the densities of portions of an object being scanned, the system further comprising:

(A) storage means for storing a set of prior estimates of the error components collected from at least one prior scan for each of said detectors at each of said projection angles, said storage means including means for receiving a new set, of estimates of the error components from a current scan and for generating an updated set of estimates as a function of the prior and new sets of estimates; and (B) ring suppression filter means for receiving the projection data signals and for generating therefrom the new set of estimates of the error components and for providing the new set of estimates to the storage means.

43. A computed tomography system for scanning objects, the system including a plurality of signal processing means, each of the processing means for generating a respective one of a plurality of projection data signals and each of the signal processing means being characterized by a respective one of a plurality of transfer functions, each of the projection data signals including a data component and an error component, the error components being representative of relative differences between the transfer functions of the plurality of processing means, the plurality of processing means generating their respective projection data signals for each scan so that the data components are representative of the densities of portions of an object being scanned, the system further comprising:

(A) storage means for storing a prior set of estimates of the error components obtained during at least one prior scan, said storage means including means for receiving a new set of estimates of the error components and for updating the set of estimates as a function of the prior set of estimates and the new sets of estimates;

(B) combining means for receiving the projection data signals of a scan and the old set of estimates and for generating a plurality of modified projection data signals as a function of the projection data signals and the old set of estimates; and (C) ring suppression filter means for receiving the modified projection data signals and for generating therefrom the new set of estimates of the error components and for applying the new set of estimates to the storage means.

* * * * *